US010939899B2

(12) United States Patent
Swift

(10) Patent No.: US 10,939,899 B2
(45) Date of Patent: Mar. 9, 2021

(54) END CAP ASSEMBLY FOR RETRACTOR AND OTHER MEDICAL DEVICES

(71) Applicant: OBP Medical Corporation, Lawrence, MA (US)

(72) Inventor: Jeffrey Ralph Swift, Boca Grande, FL (US)

(73) Assignee: OBP MEDICAL CORPORATION, Lawrence, MA (US)

( * ) Notice: Subject to any disclaimer, the term of this patent is extended or adjusted under 35 U.S.C. 154(b) by 0 days.

(21) Appl. No.: 15/869,994

(22) Filed: Jan. 12, 2018

(65) Prior Publication Data

US 2018/0177497 A1    Jun. 28, 2018

Related U.S. Application Data

(63) Continuation-in-part of application No. 15/495,371, filed on Apr. 24, 2017, which is a continuation-in-part of application No. 15/171,581, filed on Jun. 2, 2016.

(Continued)

(51) Int. Cl.
 *A61B 17/02*  (2006.01)
 *A61B 90/30*  (2016.01)
 *A61B 17/00*  (2006.01)

(52) U.S. Cl.
 CPC .............. *A61B 17/02* (2013.01); *A61B 90/30* (2016.02); *A61B 2017/00566* (2013.01);
(Continued)

(58) Field of Classification Search
 CPC .... A61B 17/02–0293; A61B 90/30–35; A61B 2218/006–008
See application file for complete search history.

(56) References Cited

U.S. PATENT DOCUMENTS

| 559,122 A | 4/1896 | Daily |
| 659,182 A | 10/1900 | Pilling |

(Continued)

FOREIGN PATENT DOCUMENTS

| CN | 2239235 Y | 11/1996 |
| CN | 2265156 Y | 10/1997 |

(Continued)

OTHER PUBLICATIONS

Pankaj Saxena, et al., Hydrodissection Technique of Harvesting Left Internal Thoracic Artery, Department of Cardiac Surgery, The Prince Charles Hospital, Chermside, Brisbane, Queensland, Australia, Thoracic Artery, Ann Thorac Surg., 2005; 80:335-6.

(Continued)

*Primary Examiner* — Eduardo C Robert
*Assistant Examiner* — Steven J Cotroneo
(74) *Attorney, Agent, or Firm* — Cowan, Liebowitz & Latman, P.C.; Anastasia Zhadina

(57) ABSTRACT

An illuminated medical device, comprising a blade portion having a proximal end and a distal end, the blade portion comprising an operative portion at the distal end, a handle portion connected to the proximal end of the blade portion, the handle portion having a hollow cross-section and an open bottom end, an illumination assembly comprising at least one light source, an activation device for energizing the light source, and at least one battery for powering the light source, and an end cap assembly coupled to the open bottom end of the handle portion and accommodating the activation device and the at least one battery therein. In the illuminated medical device, a portion of the activation device extends through an opening in the end cap assembly and the at least one battery is held by the end cap assembly to overlap with the activation device and the opening in the end cap assembly.

22 Claims, 41 Drawing Sheets

Related U.S. Application Data

(60) Provisional application No. 62/258,806, filed on Nov. 23, 2015, provisional application No. 62/170,280, filed on Jun. 3, 2015.

(52) U.S. Cl.
CPC ........... *A61B 2017/00734* (2013.01); *A61B 2017/00831* (2013.01); *A61B 2017/00929* (2013.01); *A61B 2217/005* (2013.01); *A61B 2218/008* (2013.01)

(56) References Cited

U.S. PATENT DOCUMENTS

| | | |
|---|---|---|
| 2,235,979 A | 3/1941 | Brown |
| 2,247,458 A | 6/1941 | Shepard |
| 2,482,971 A | 9/1949 | Golson |
| 2,592,190 A | 4/1952 | Rubens et al. |
| 3,324,850 A | 6/1967 | Gunning et al. |
| 3,332,414 A | 7/1967 | Gasper |
| 3,532,088 A | 10/1970 | Fiore |
| 3,592,199 A * | 7/1971 | Ostensen ............. A61B 1/267 600/198 |
| 3,595,222 A | 7/1971 | Vellacott |
| 3,638,644 A * | 2/1972 | Reick .................. A61B 1/267 600/191 |
| 3,675,641 A | 7/1972 | Fiore |
| 3,716,047 A | 2/1973 | Moore et al. |
| 3,729,006 A | 4/1973 | Wilder et al. |
| 3,762,400 A | 10/1973 | McDonald |
| 3,769,968 A | 11/1973 | Blount et al. |
| 3,789,835 A | 2/1974 | Whitman |
| 3,815,585 A | 6/1974 | Fiore |
| 3,826,248 A * | 7/1974 | Gobels ................. A61B 1/267 600/193 |
| 3,851,642 A | 12/1974 | McDonald |
| 3,934,578 A | 1/1976 | Heine |
| 3,945,371 A | 3/1976 | Adelman |
| 3,978,850 A | 9/1976 | Moore et al. |
| 4,067,323 A | 1/1978 | Troutner |
| 4,156,424 A | 5/1979 | Burgin |
| 4,210,133 A | 7/1980 | Castaneda |
| 4,226,228 A | 10/1980 | Shin et al. |
| 4,263,899 A | 4/1981 | Burgin |
| 4,300,541 A | 11/1981 | Burgin |
| 4,337,763 A | 7/1982 | Petrassevich |
| 4,432,351 A | 2/1984 | Hoary |
| 4,492,220 A | 1/1985 | Hayes |
| 4,502,468 A | 3/1985 | Burgin |
| 4,527,553 A | 7/1985 | Upsher |
| 4,546,761 A | 10/1985 | McCullough |
| 4,551,129 A | 11/1985 | Coleman et al. |
| 4,562,832 A | 1/1986 | Wilder |
| 4,566,439 A | 1/1986 | Burgin |
| 4,574,784 A | 3/1986 | Soloway |
| 4,597,383 A | 7/1986 | Van Der Bel |
| 4,607,623 A | 8/1986 | Bauman |
| 4,619,248 A | 10/1986 | Walsh |
| 4,638,792 A | 1/1987 | Burgin |
| 4,766,887 A | 8/1988 | Cecil, Jr. et al. |
| 4,807,600 A | 2/1989 | Hayes |
| 4,884,559 A | 12/1989 | Collins |
| 4,905,670 A | 3/1990 | Adair |
| 4,934,352 A | 6/1990 | Sullivan, Jr. |
| 4,971,036 A | 11/1990 | Collins |
| 5,018,507 A | 5/1991 | Montaldi |
| 5,026,368 A | 6/1991 | Adair |
| 5,054,906 A | 10/1991 | Lyons, Jr. |
| 5,063,908 A | 11/1991 | Collins |
| 5,143,054 A | 9/1992 | Adair |
| 5,165,387 A | 11/1992 | Woodson |
| 5,174,278 A | 12/1992 | Babkow |
| 5,179,937 A | 1/1993 | Lee |
| 5,179,938 A | 1/1993 | Lonky |
| 5,222,271 A | 6/1993 | Eganhouse |
| D337,384 S | 7/1993 | Schucman |
| 5,318,009 A | 6/1994 | Robinson |
| 5,329,938 A | 7/1994 | Lonky |
| 5,427,152 A | 6/1995 | Weber |
| 5,438,976 A | 8/1995 | Nash |
| 5,465,709 A | 11/1995 | Dickie et al. |
| 5,499,964 A | 3/1996 | Beck et al. |
| 5,512,038 A | 4/1996 | O'Neal et al. |
| 5,553,627 A | 9/1996 | Newkirk |
| 5,695,492 A | 12/1997 | Brown |
| 5,716,329 A | 2/1998 | Dieter |
| 5,785,648 A | 7/1998 | Min |
| 5,840,013 A | 11/1998 | Lee et al. |
| 5,846,249 A | 12/1998 | Thompson |
| 5,865,729 A | 2/1999 | Meehan |
| 5,873,820 A | 2/1999 | Norell |
| 5,879,304 A | 3/1999 | Schuchman et al. |
| 5,888,195 A | 3/1999 | Schneider |
| 5,899,854 A | 5/1999 | Slishman |
| 5,916,150 A | 6/1999 | Sillman |
| 5,967,971 A | 10/1999 | Bolser |
| 6,001,077 A | 12/1999 | Ellman et al. |
| 6,004,265 A | 12/1999 | Hsu et al. |
| 6,036,638 A | 3/2000 | Nwawka |
| 6,036,713 A | 3/2000 | Kieturakis |
| 6,048,308 A | 4/2000 | Strong |
| 6,080,105 A | 6/2000 | Spears |
| 6,130,520 A | 10/2000 | Wawro et al. |
| 6,176,824 B1 | 1/2001 | Davis |
| 6,186,944 B1 | 2/2001 | Tsai |
| 6,217,512 B1 | 4/2001 | Salo et al. |
| 6,231,505 B1 | 5/2001 | Martin |
| 6,231,506 B1 | 5/2001 | Hu et al. |
| 6,254,247 B1 | 7/2001 | Carson |
| 6,277,067 B1 | 8/2001 | Blair |
| 6,319,199 B1 | 11/2001 | Sheehan et al. |
| 6,346,085 B1 | 2/2002 | Schiffman |
| 6,359,644 B1 | 3/2002 | Salvati |
| 6,361,489 B1 | 3/2002 | Tsai |
| 6,379,296 B1 | 4/2002 | Baggett |
| 6,379,299 B1 | 4/2002 | Borodulin et al. |
| 6,394,111 B1 | 5/2002 | Jacobs et al. |
| 6,394,950 B1 | 5/2002 | Weiss |
| 6,413,208 B1 | 7/2002 | Schöllhorn et al. |
| 6,416,465 B2 | 7/2002 | Brau |
| 6,428,180 B1 | 8/2002 | Karram et al. |
| 6,432,045 B2 | 8/2002 | Lemperle et al. |
| 6,432,049 B1 | 8/2002 | Banta |
| 6,436,033 B2 | 8/2002 | Tan |
| 6,450,952 B1 | 9/2002 | Rioux |
| 6,468,206 B1 | 10/2002 | Hipps et al. |
| 6,468,232 B1 | 10/2002 | Ashton-Miller et al. |
| 6,487,440 B2 | 11/2002 | Deckert et al. |
| 6,504,985 B2 | 1/2003 | Parker et al. |
| 6,523,973 B2 | 2/2003 | Galli |
| 6,524,259 B2 | 2/2003 | Baxter-Jones et al. |
| 6,569,091 B2 | 5/2003 | Diokno et al. |
| 6,589,168 B2 | 7/2003 | Thompson |
| 6,595,917 B2 | 7/2003 | Nieto |
| 6,616,603 B1 | 9/2003 | Fontana |
| 6,626,825 B2 | 9/2003 | Tsai |
| 6,663,576 B2 | 12/2003 | Gombrich et al. |
| 6,676,598 B2 | 1/2004 | Rudischhauser et al. |
| 6,719,688 B2 | 4/2004 | Pecherer et al. |
| 6,761,687 B1 | 7/2004 | Doshi |
| 6,830,547 B2 | 12/2004 | Weiss |
| 6,896,653 B1 | 5/2005 | Vail, III et al. |
| 7,014,340 B2 | 3/2006 | Betis |
| 7,029,439 B2 | 4/2006 | Roberts et al. |
| D520,464 S | 5/2006 | Strong |
| 7,223,223 B2 | 5/2007 | Lindsay |
| 7,276,025 B2 | 10/2007 | Roberts et al. |
| 7,306,559 B2 | 12/2007 | Williams |
| 7,492,116 B2 | 2/2009 | Oleynikov et al. |
| 7,631,981 B2 | 12/2009 | Miller et al. |
| 7,736,304 B2 | 6/2010 | Pecherer |
| 7,758,203 B2 | 7/2010 | McMahon et al. |
| 7,878,973 B2 | 2/2011 | Yee et al. |
| 7,909,759 B2 | 3/2011 | Pecherer |

(56) References Cited

U.S. PATENT DOCUMENTS

| | | |
|---|---|---|
| 7,967,809 B2 | 6/2011 | Jay-Robinson |
| 8,012,089 B2 * | 9/2011 | Bayat .................... A61B 17/02 600/214 |
| 8,047,987 B2 | 11/2011 | Grey et al. |
| 8,052,702 B2 | 11/2011 | Hess et al. |
| 8,088,066 B2 | 1/2012 | Grey et al. |
| 8,096,945 B2 | 1/2012 | Buchok et al. |
| 8,142,352 B2 * | 3/2012 | Vivenzio ................ A61B 1/303 600/186 |
| 8,142,353 B2 | 3/2012 | Pecherer et al. |
| 8,157,728 B2 | 4/2012 | Danna et al. |
| 8,162,826 B2 | 4/2012 | Pecherer et al. |
| 8,251,898 B2 | 8/2012 | Pecherer |
| 8,292,805 B2 | 10/2012 | Vayser et al. |
| 8,317,693 B2 | 11/2012 | Grey et al. |
| 8,388,523 B2 | 3/2013 | Vivenzio et al. |
| 8,394,017 B2 | 3/2013 | Kieffer |
| 8,435,175 B2 | 5/2013 | McMahon et al. |
| 8,512,234 B2 | 8/2013 | Grey et al. |
| 8,512,237 B2 | 8/2013 | Bastia |
| 8,555,892 B2 | 10/2013 | Traub |
| 8,596,847 B2 | 12/2013 | Vayser et al. |
| 8,628,879 B2 | 1/2014 | Pecherer et al. |
| 8,651,704 B1 | 2/2014 | Gordin et al. |
| 8,795,162 B2 | 8/2014 | Vayser et al. |
| 8,821,385 B2 | 9/2014 | Naito |
| 8,870,761 B2 | 10/2014 | Vayser et al. |
| D719,652 S | 12/2014 | Swift |
| 8,979,745 B2 | 3/2015 | Swift |
| 9,044,161 B2 | 6/2015 | Vayser et al. |
| 9,050,048 B2 | 6/2015 | Nadershahi |
| 9,072,452 B2 | 7/2015 | Vayser et al. |
| D745,669 S | 12/2015 | Swift |
| 9,241,617 B2 | 1/2016 | Grey et al. |
| D752,217 S | 3/2016 | Swift |
| 9,271,709 B2 | 3/2016 | Grey et al. |
| 9,271,710 B2 | 3/2016 | Grey et al. |
| 9,282,878 B2 | 3/2016 | Grey et al. |
| D753,295 S | 4/2016 | Vivenzio et al. |
| 9,307,897 B2 | 4/2016 | Swift |
| 9,308,054 B2 | 4/2016 | Vayser et al. |
| 9,332,898 B2 | 5/2016 | McMahon et al. |
| 9,468,366 B2 | 10/2016 | Grey et al. |
| 9,510,737 B2 | 12/2016 | Vayser et al. |
| 9,532,706 B2 | 1/2017 | McMahon et al. |
| 9,629,529 B1 | 4/2017 | Indovina et al. |
| 9,636,182 B2 | 5/2017 | Vayser et al. |
| 9,718,130 B1 | 8/2017 | Vayser et al. |
| 9,763,743 B2 | 9/2017 | Lin et al. |
| 9,808,231 B2 | 11/2017 | Miraki et al. |
| 9,814,377 B2 | 11/2017 | Lia et al. |
| 9,820,638 B2 | 11/2017 | Cheng |
| 9,820,729 B2 | 11/2017 | Miles et al. |
| 9,826,892 B2 | 11/2017 | Dresher et al. |
| 9,833,295 B2 | 12/2017 | Vayser et al. |
| 9,833,308 B2 | 12/2017 | Dye |
| 9,844,364 B2 | 12/2017 | Grey et al. |
| 9,861,349 B2 | 1/2018 | Nadershahi et al. |
| 9,867,531 B2 | 1/2018 | Pacey et al. |
| 9,877,639 B2 | 1/2018 | Grey et al. |
| 9,877,644 B2 | 1/2018 | Greenstein et al. |
| D809,660 S | 2/2018 | Nguyen et al. |
| 9,883,792 B2 | 2/2018 | McMahon et al. |
| 9,888,957 B2 | 2/2018 | Wolf et al. |
| 9,907,544 B2 | 3/2018 | Nadershahi et al. |
| 9,913,682 B2 | 3/2018 | Wolf et al. |
| 9,918,618 B2 | 3/2018 | Molnar |
| 9,918,802 B2 | 3/2018 | Coppersmith et al. |
| 9,931,028 B2 | 4/2018 | Lia et al. |
| 9,943,295 B2 | 4/2018 | King |
| 9,949,814 B2 | 4/2018 | Alexander et al. |
| 9,955,858 B2 | 5/2018 | Pamnani et al. |
| 9,968,262 B2 | 5/2018 | Greenstein et al. |
| 9,968,346 B2 | 5/2018 | Alexander et al. |
| 9,980,710 B2 | 5/2018 | Seifert et al. |
| 9,986,901 B2 | 6/2018 | Grey et al. |
| 9,986,903 B2 | 6/2018 | Nadershahi et al. |
| 9,986,988 B2 | 6/2018 | Ferro et al. |
| 9,999,345 B2 | 6/2018 | Vayser et al. |
| 10,004,392 B2 | 6/2018 | Millard et al. |
| 10,004,393 B2 | 6/2018 | Kucklick |
| 10,028,648 B2 | 7/2018 | Goldfain et al. |
| 10,028,649 B2 | 7/2018 | Salvati et al. |
| 10,028,780 B2 | 7/2018 | Wolf et al. |
| 10,045,686 B2 | 8/2018 | Ou Yang et al. |
| 10,045,731 B2 | 8/2018 | Prasad et al. |
| 10,052,432 B2 | 8/2018 | Dexter et al. |
| 10,064,611 B2 | 9/2018 | Ross et al. |
| 10,064,613 B2 | 9/2018 | Davis et al. |
| 10,068,173 B2 | 9/2018 | Vayser et al. |
| 10,092,176 B2 | 10/2018 | Kienzle et al. |
| 10,092,281 B2 | 10/2018 | Perler et al. |
| 10,098,530 B2 | 10/2018 | McMahon et al. |
| 10,105,043 B2 | 10/2018 | George |
| 10,117,646 B2 | 11/2018 | Friedrich et al. |
| 10,130,441 B2 | 11/2018 | Martinez |
| 10,166,016 B2 | 1/2019 | Shimizu et al. |
| 10,172,601 B2 | 1/2019 | Ann |
| 10,174,933 B2 | 1/2019 | Phillips, Jr. et al. |
| 10,188,298 B2 | 1/2019 | Greenstein et al. |
| 10,213,271 B2 | 2/2019 | Duggal et al. |
| 10,219,800 B2 | 3/2019 | Tsubouchi |
| 10,220,445 B2 | 3/2019 | Vayser et al. |
| 10,226,555 B2 | 3/2019 | Vayser et al. |
| 10,238,462 B2 | 3/2019 | Wood et al. |
| D846,119 S | 4/2019 | Greeley et al. |
| 10,278,571 B2 | 5/2019 | Poormand |
| 10,292,782 B2 | 5/2019 | Haverich et al. |
| 10,292,784 B2 | 5/2019 | Duggal et al. |
| 10,342,525 B2 | 7/2019 | Wilson |
| 2001/0029044 A1 | 10/2001 | Gombrich et al. |
| 2002/0022769 A1 | 2/2002 | Smith et al. |
| 2002/0038075 A1 | 3/2002 | Tsai |
| 2002/0038076 A1 | 3/2002 | Sheehan et al. |
| 2002/0055670 A1 | 5/2002 | Weiss |
| 2002/0115909 A1 | 8/2002 | Bolser |
| 2002/0156350 A1 | 10/2002 | Nieto |
| 2002/0165435 A1 | 11/2002 | Weiss |
| 2002/0198471 A1 | 12/2002 | Baxter-Jones et al. |
| 2003/0095781 A1 | 5/2003 | Williams |
| 2003/0105387 A1 | 6/2003 | Frumovitz et al. |
| 2003/0139673 A1 | 7/2003 | Vivenzio et al. |
| 2003/0158502 A1 | 8/2003 | Baxter-Jones et al. |
| 2003/0176772 A1 | 9/2003 | Yang |
| 2003/0187331 A1 | 10/2003 | Faludi et al. |
| 2004/0026829 A1 | 2/2004 | Van Der Weegen |
| 2004/0054260 A1 | 3/2004 | Klaassen et al. |
| 2004/0141175 A1 | 7/2004 | Baldwin et al. |
| 2004/0183482 A1 | 9/2004 | Roberts et al. |
| 2004/0184288 A1 | 9/2004 | Bettis |
| 2004/0186355 A1 | 9/2004 | Strong |
| 2005/0065496 A1 | 3/2005 | Simon et al. |
| 2005/0085699 A1 | 4/2005 | Weiss |
| 2005/0085723 A1 | 4/2005 | Huebner |
| 2005/0093718 A1 | 5/2005 | Martin |
| 2005/0125015 A1 | 6/2005 | McNally-Heintzelman et al. |
| 2005/0159649 A1 | 7/2005 | Patel |
| 2005/0192482 A1 | 9/2005 | Carpenter |
| 2005/0215858 A1 | 9/2005 | Vail, III |
| 2005/0240081 A1 | 10/2005 | Eliachar |
| 2005/0277811 A1 | 12/2005 | Richards et al. |
| 2006/0084843 A1 | 4/2006 | Sommerich et al. |
| 2006/0155276 A1 | 7/2006 | Walulik et al. |
| 2006/0189847 A1 | 8/2006 | Yee et al. |
| 2006/0200186 A1 | 9/2006 | Marchek et al. |
| 2007/0043264 A1 | 2/2007 | Gillis et al. |
| 2007/0060795 A1 | 3/2007 | Vayser et al. |
| 2007/0060938 A1 | 3/2007 | Dziadik et al. |
| 2007/0066872 A1 | 3/2007 | Morrison et al. |
| 2007/0100212 A1 | 5/2007 | Pimenta et al. |
| 2007/0208226 A1 | 9/2007 | Grey et al. |
| 2007/0230164 A1 | 10/2007 | Vivenzio et al. |
| 2007/0230167 A1 | 10/2007 | McMahon et al. |
| 2007/0255110 A1 | 11/2007 | Wax et al. |

(56) References Cited

U.S. PATENT DOCUMENTS

| | | |
|---|---|---|
| 2007/0270866 A1 | 11/2007 | Von Jako |
| 2007/0287888 A1 | 12/2007 | Lovell et al. |
| 2008/0002426 A1 | 1/2008 | Vayser et al. |
| 2008/0113312 A1 | 5/2008 | Ortega |
| 2008/0221569 A1 | 9/2008 | Moore et al. |
| 2008/0228038 A1 | 9/2008 | McMahon et al. |
| 2008/0269564 A1 | 10/2008 | Gelnett |
| 2008/0269565 A1 | 10/2008 | McMahon et al. |
| 2008/0278936 A1 | 11/2008 | Kurth et al. |
| 2009/0018400 A1 | 1/2009 | Raymond et al. |
| 2009/0069634 A1 | 3/2009 | Larkin |
| 2009/0097236 A1 | 4/2009 | Miller et al. |
| 2009/0112068 A1 | 4/2009 | Grey et al. |
| 2009/0275603 A1 | 11/2009 | Krauter et al. |
| 2009/0287192 A1 | 11/2009 | Vivenzio et al. |
| 2009/0312610 A1 | 12/2009 | Buchok et al. |
| 2010/0036382 A1 | 2/2010 | Bonnadier |
| 2010/0041955 A1 | 2/2010 | Grey et al. |
| 2010/0097794 A1 | 4/2010 | Teng et al. |
| 2010/0190129 A1 | 7/2010 | Paz |
| 2010/0191062 A1 | 7/2010 | Kieffer |
| 2010/0292533 A1 | 11/2010 | Kasahara et al. |
| 2011/0022032 A1 | 1/2011 | Zemlok et al. |
| 2011/0275894 A1 | 11/2011 | Mackin |
| 2012/0055470 A1 | 3/2012 | Pecherer et al. |
| 2012/0059226 A1 | 3/2012 | Funt |
| 2012/0078060 A1 | 3/2012 | Swift |
| 2012/0116170 A1 | 5/2012 | Vayser et al. |
| 2012/0232352 A1 | 9/2012 | Lin et al. |
| 2013/0018230 A1 | 1/2013 | Su et al. |
| 2013/0021798 A1 | 1/2013 | Chen et al. |
| 2013/0041229 A2 | 2/2013 | Hahn et al. |
| 2013/0092421 A1 | 4/2013 | Kajiya |
| 2013/0102850 A1 | 4/2013 | Fiorella |
| 2013/0102887 A1 | 4/2013 | Thompson et al. |
| 2013/0109910 A1 | 5/2013 | Alexander et al. |
| 2013/0158345 A1 | 6/2013 | Majlessi |
| 2013/0197313 A1 | 8/2013 | Wan |
| 2013/0245657 A1 | 9/2013 | Deville et al. |
| 2013/0267786 A1 | 10/2013 | Vayser et al. |
| 2013/0281784 A1 | 10/2013 | Ray |
| 2013/0324801 A1 | 12/2013 | Grey et al. |
| 2014/0088371 A1 | 3/2014 | Vayser et al. |
| 2014/0179998 A1 | 6/2014 | Pacey |
| 2014/0202459 A1 | 7/2014 | Iqbal |
| 2014/0228875 A1 | 8/2014 | Saadat |
| 2014/0257039 A1 | 9/2014 | Feldman |
| 2014/0275790 A1 | 9/2014 | Vivenzio et al. |
| 2014/0309499 A1 | 10/2014 | Swift |
| 2014/0316211 A1 | 10/2014 | Hermle |
| 2014/0323800 A1 | 10/2014 | Dye |
| 2014/0364695 A1 | 12/2014 | Nadershahi et al. |
| 2014/0371536 A1 | 12/2014 | Miller et al. |
| 2015/0018625 A1 | 1/2015 | Miraki et al. |
| 2015/0157469 A1 | 6/2015 | Prado et al. |
| 2015/0238070 A1 | 8/2015 | Lia et al. |
| 2015/0297217 A1 | 10/2015 | Huitema et al. |
| 2016/0000305 A1 | 1/2016 | Elbaz et al. |
| 2016/0038032 A1 | 2/2016 | Dan |
| 2016/0066915 A1 | 3/2016 | Baber et al. |
| 2016/0081833 A1 | 3/2016 | Leblanc et al. |
| 2016/0095506 A1 | 4/2016 | Dan et al. |
| 2016/0100751 A1 | 4/2016 | Davis et al. |
| 2016/0151058 A1 | 6/2016 | Ferro et al. |
| 2016/0302657 A1 | 10/2016 | Hussey et al. |
| 2017/0007228 A1 | 1/2017 | Costabile |
| 2017/0020621 A1 | 1/2017 | Huldin et al. |
| 2017/0059400 A1 | 3/2017 | Murphy et al. |
| 2017/0065282 A1 | 3/2017 | Mathis et al. |
| 2017/0079518 A1 | 3/2017 | Elbaz et al. |
| 2017/0172404 A1 | 6/2017 | McMahon et al. |
| 2017/0172555 A1 | 6/2017 | Shimizu et al. |
| 2017/0181605 A1 | 6/2017 | Lalli et al. |
| 2017/0181607 A1 | 6/2017 | Lalli et al. |
| 2017/0181615 A1 | 6/2017 | Vella et al. |
| 2017/0181616 A1 | 6/2017 | Vella et al. |
| 2017/0224206 A1 | 8/2017 | Vayser |
| 2017/0231712 A1 | 8/2017 | Vayser |
| 2017/0300623 A1 | 10/2017 | Rosenblatt et al. |
| 2017/0303903 A1 | 10/2017 | De Koning et al. |
| 2017/0347871 A1 | 12/2017 | Wallace et al. |
| 2017/0360423 A1 | 12/2017 | Stevenson et al. |
| 2018/0000469 A1 | 1/2018 | Wood et al. |
| 2018/0008137 A1 | 1/2018 | Poormand |
| 2018/0008138 A1 | 1/2018 | Thommen et al. |
| 2018/0008368 A1 | 1/2018 | Duggal et al. |
| 2018/0014721 A1 | 1/2018 | Rullo et al. |
| 2018/0014842 A1 | 1/2018 | Shener-Irmakoglu |
| 2018/0014900 A1 | 1/2018 | Vayser et al. |
| 2018/0036095 A1 | 2/2018 | Vayser et al. |
| 2018/0042596 A1 | 2/2018 | Tsubouchi |
| 2018/0064316 A1 | 3/2018 | Charles et al. |
| 2018/0064317 A1 | 3/2018 | Tesar |
| 2018/0078301 A1 | 3/2018 | Vayser |
| 2018/0116581 A1 | 5/2018 | Prasad et al. |
| 2018/0125336 A1 | 5/2018 | Goldfarb et al. |
| 2018/0125347 A1 | 5/2018 | Czyzewski et al. |
| 2018/0132710 A1 | 5/2018 | Pacey et al. |
| 2018/0132970 A1 | 5/2018 | Ritter |
| 2018/0153391 A1 | 6/2018 | McMahon et al. |
| 2018/0156448 A1 | 6/2018 | Phillips, Jr. et al. |
| 2018/0206832 A1 | 7/2018 | Greeley et al. |
| 2018/0228376 A1 | 8/2018 | Greenstein et al. |
| 2018/0228483 A1 | 8/2018 | Duggal et al. |
| 2018/0235444 A1 | 8/2018 | Tsai |
| 2018/0235592 A1 | 8/2018 | Kass et al. |
| 2018/0249902 A1 | 9/2018 | Grey et al. |
| 2018/0263480 A1 | 9/2018 | Lalli et al. |
| 2018/0271581 A1 | 9/2018 | Ou Yang et al. |
| 2018/0280011 A1 | 10/2018 | Ferro et al. |
| 2018/0296082 A1 | 10/2018 | Salvati et al. |
| 2018/0317746 A1 | 11/2018 | Lalli et al. |
| 2018/0317752 A1 | 11/2018 | Cybulski et al. |
| 2018/0317902 A1 | 11/2018 | Green et al. |
| 2018/0328572 A1 | 11/2018 | Kennedy et al. |
| 2018/0336474 A1 | 11/2018 | Vayser et al. |
| 2018/0344144 A1 | 12/2018 | Bouquet |
| 2018/0353059 A1 | 12/2018 | Tesar |
| 2018/0360301 A1 | 12/2018 | Kucklick |
| 2019/0038273 A1 | 2/2019 | Perler et al. |
| 2019/0049655 A1 | 2/2019 | Zagatsky et al. |
| 2019/0076138 A1 | 3/2019 | Opperman |
| 2019/0083079 A1 | 3/2019 | Shimizu et al. |
| 2019/0133432 A1 | 5/2019 | Tsai |
| 2019/0143006 A1 | 5/2019 | Vayser et al. |
| 2019/0143414 A1 | 5/2019 | Vayser et al. |
| 2019/0150422 A1 | 5/2019 | Welch |
| 2019/0150725 A1 | 5/2019 | Ramanujam et al. |
| 2019/0150739 A1 | 5/2019 | Wawro et al. |
| 2019/0150786 A1 | 5/2019 | Vassallo et al. |
| 2019/0167111 A1 | 6/2019 | Greenstein et al. |
| 2019/0167378 A1 | 6/2019 | Wood et al. |
| 2019/0190293 A1 | 6/2019 | Wawro et al. |
| 2019/0223708 A1 | 7/2019 | Recanati et al. |
| 2019/0254512 A1 | 8/2019 | Spiertz |
| 2019/0335988 A1 | 11/2019 | Lia et al. |
| 2019/0343379 A1 | 11/2019 | Altamura |
| 2019/0365217 A1 | 12/2019 | Hegenberger |
| 2020/0008694 A1 | 1/2020 | Karla et al. |
| 2020/0046216 A1 | 2/2020 | Moein |
| 2020/0069171 A1 | 3/2020 | Miller et al. |
| 2020/0107714 A1 | 4/2020 | Bar-Or et al. |
| 2020/0253467 A1 | 8/2020 | Lees, Jr. et al. |
| 2020/0337541 A1 | 10/2020 | Vivenzio et al. |

FOREIGN PATENT DOCUMENTS

| | | |
|---|---|---|
| CN | 2516109 Y | 10/2002 |
| CN | 2629738 Y | 8/2004 |
| CN | 1565664 A | 1/2005 |
| CN | 2668152 Y | 1/2005 |
| CN | 1717195 A | 1/2006 |
| CN | 101179982 A | 5/2008 |
| CN | 201055387 Y | 5/2008 |

(56) References Cited

FOREIGN PATENT DOCUMENTS

| | | |
|---|---|---|
| CN | 102415869 A | 4/2012 |
| CN | 302536685 S | 8/2013 |
| CN | 203591245 U | 5/2014 |
| CN | 103925266 A | 7/2014 |
| CN | 203898367 U | 10/2014 |
| CN | 102573700 B | 12/2014 |
| DE | 2128855 A | 12/1972 |
| DE | 202004002963 U1 | 5/2004 |
| DE | 202005019780 U1 | 5/2006 |
| DE | 600 33 612 T2 | 12/2007 |
| DE | 202010017638 U | 5/2012 |
| EP | 0190014 A2 | 8/1986 |
| EP | 1074224 A2 | 7/2001 |
| FR | 2490478 A1 | 3/1982 |
| GB | 2505463 A | 5/2014 |
| RU | 2187972 C2 | 8/2002 |
| RU | 2308873 C2 | 10/2007 |
| WO | 9825512 A1 | 6/1998 |
| WO | 0137739 A1 | 5/2001 |
| WO | 01/62137 A2 | 8/2001 |
| WO | 03082123 A2 | 10/2003 |
| WO | 2004064624 A1 | 8/2004 |
| WO | 2006107877 A2 | 10/2006 |
| WO | 2006107878 A2 | 10/2006 |
| WO | 2009137017 A2 | 11/2009 |
| WO | 2013-044151 A1 | 3/2013 |
| WO | 2014-041172 A1 | 3/2014 |
| WO | 2006121530 A2 | 11/2016 |

OTHER PUBLICATIONS

International Search Report of PCT/US2016/035508, dated Jan. 3, 2019.
The above documents were cited in a European Search Report dated Nov. 23, 2018, that issued in the corresponding European Patent Application No. 16747107.7.
The above patent was cited in a Oct. 29, 2018 Chinese Office Action, which is enclosed without an English Translation, that issued in Chinese Patent Application No. 201711159829.6.
The above foreign patent documents were cited in a Nov. 1, 2017 Chinese Office Action, which is enclosed without an English Translation, that issued in Chinese Patent Application No. 2017102800054450.
Solvey, Techinical Data Sheet, Ixef 1022 polyarylamide, Feb. 13, 2015, pp. 1-5.
http://www.makeitfrom.com/material-properties/Polyetheretheketone-PEEK, printed on Oct. 9, 2016, pp. 1-9.
International Search Report for International application No. PCT/US2016/016154 dated May 19, 2016 for corresponding U.S. application, U.S. Appl. No. 14/614,413.
International Search Report, for International application No. PCT/US2016/035508 dated Sep. 15, 2016 for corresponding U.S. application, U.S. Appl. No. 15/171,581.
International Search Report for International application No. PCT/US2016/036833 dated Jan. 19, 2017.
U.S. Patent references 121-125 and U.S. Published Patent Application references 48 and 50 were cited in an Office Action issued in U.S. Appl. No. 15/171,581.
U.S. Published Patent Application references 47, 49 and 51 were cited in a PCT Search Report issued in PCT Application No. PCT/US2017/042617.
The above foreign patent document 1 was cited in the Jul. 16, 2018 Chinese Office Action, which is enclosed without an English Translation, that issued in Chinese Patent Application No. 201510543086.7.
International Search Report of PCT/US2018/020644 dated Mar. 2, 2018.
The above U.S. Publications documents #1 and #2 were cited in a Supplementary European Search Report dated Apr. 24, 2019, which is enclosed, that issued in European Patent Application No. 16804432.9.
Redefining illumination, Eikon LT Adapt SE For optimal precision and protection (2019), Stryker, www.stryker.com/surgical (3 pages).

* cited by examiner

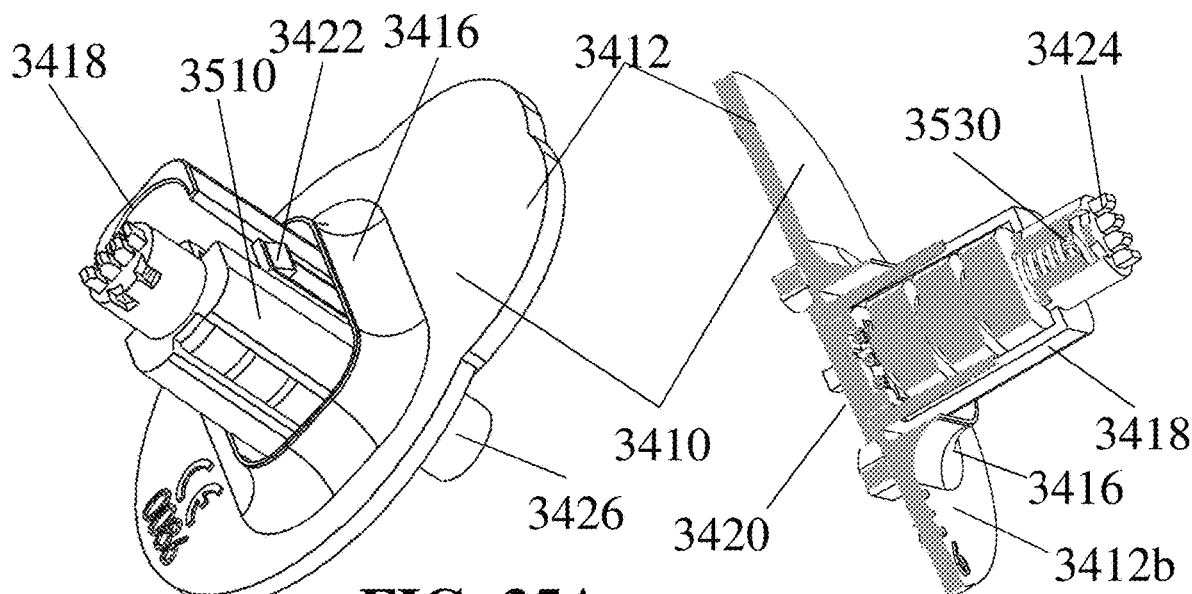
FIG. 35A
FIG. 35B
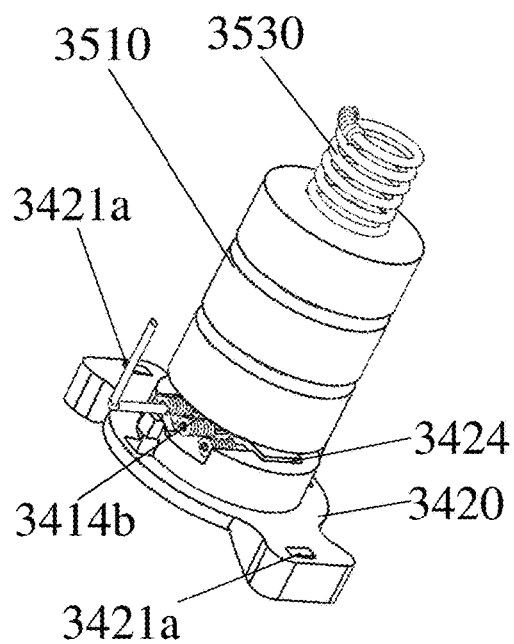
FIG. 36A
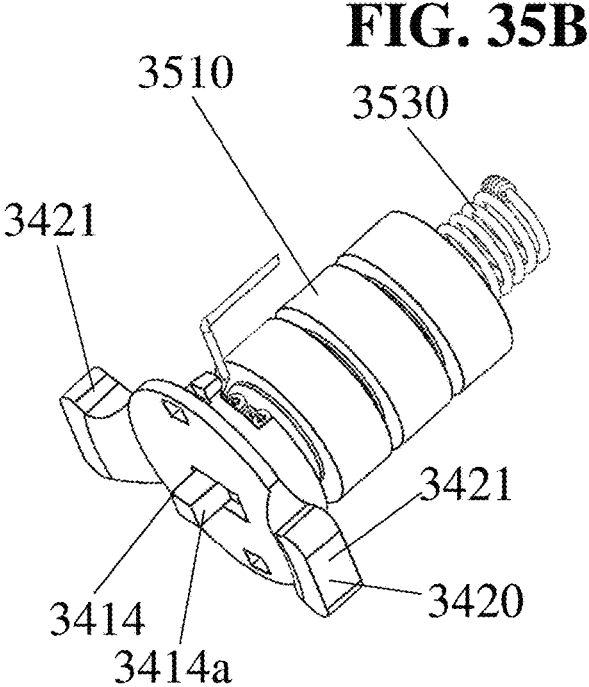
FIG. 36B

END CAP ASSEMBLY FOR RETRACTOR AND OTHER MEDICAL DEVICES

CROSS-REFERENCE TO RELATED APPLICATIONS

This application is a continuation-in-part of U.S. patent application Ser. No. 15/495,371, filed on Apr. 24, 2017 and entitled "Retractor," which is a continuation-in-part application of U.S. patent application Ser. No. 15/171,581, filed on Jun. 2, 2016 and entitled "Retractor," which claims priority to U.S. Provisional Patent Application Ser. No. 62/170,280, filed on Jun. 3, 2015, and entitled "Surgical Instrument" and to U.S. Provisional Patent Application Ser. No. 62/258,806, filed on Nov. 23, 2015, and entitled "Retractor." The entire contents of each of those applications are incorporated herein by reference.

INTRODUCTION

Embodiments described herein relate to surgical instrumentation and, more particularly, a retractor providing an integrated light source and rounded blade, forming an unobstructed, illuminated viewing slot for the physician's field of view.

Light sources that interfere with the physicians field of view, or that do not properly illuminate the field of view, inhibit the physician from seeing critical developments. For example, when performing a dissection, potential blood sources may drain blood into the dissection cavity, and without proper treatment, these blood sources can cause post-surgery infection. Such concerns are pertinent when using breast retractors, which are used for breast augmentation or reconstruction.

Conventional breast retractors may cause blood to drain into the dissection cavity due to a lack of proper illumination in the field of view.

Currently, breast retractors require substantial auxiliary lighting. This lighting is expensive, difficult to assemble, requires cleaning and reprocessing after each use, and due to lack of customization for breast retractors, fails to provide sufficient light at desired locations. Namely, practitioners must assemble and secure an independent light source onto the breast retractor prior to the patient procedure. These auxiliary light sources do not provide the physician with the ability to focus the light onto, and illuminate, specific portions of the surgical field without interfering with the physician's field of view.

Further, auxiliary light sources affixed to a retractor require expensive preparation and components that must be reprocessed after each patient procedure in order to ensure no patient cross-contamination. Without adequate reprocessing, cross contamination from one patient to another can occur. Moreover, even with reprocessing of the light sources, effective reprocessing is not 100% guaranteed, and many hospitals have reported patient cross-contamination due to inadequate or errors in reprocessing.

Therefore, as can be seen, there is a need for a retractor providing an integrated light source and rounded blade forming an unobstructed, illuminated viewing slot for the physician's field of view.

One exemplary aspect comprises an illuminated surgical retractor, comprising: a blade having a top surface and a bottom surface; a handle extending at an angle from a proximal end of the blade; a curved section connecting the handle to the blade; and an illumination assembly comprising at least one light source, at least one battery and an activation device for energizing the light source, and the illumination assembly being permanently attached to the retractor, wherein the blade, handle, and curved section are molded from a glass-fiber reinforced polymer.

One exemplary aspect comprises an illuminated surgical retractor, comprising: a blade having a top surface and a bottom surface; a handle extending at an angle from a proximal end of the blade; a curved section connecting the handle to the blade; and an illumination assembly comprising at least one light source, at least one battery and an activation device for energizing the light source, and the illumination assembly being permanently attached to the retractor; wherein the blade, handle, and curved section are molded from a low conductivity polymer.

One exemplary aspect comprises an illuminated surgical retractor, comprising: a blade having a top surface and a bottom surface; a handle extending at an angle from a proximal end of the blade; a curved section connecting the handle to the blade; and an illumination assembly comprising at least one light source, at least one battery and an activation device for energizing the light source, and the illumination assembly being permanently attached to the curved section; wherein the blade, handle, and curved section are molded from a radiolucent polymer.

In various embodiments: (1) the polymer is a 50% glass-fiber reinforced polymer; (2) the polymer is a polyarylamide compound; (3) the polymer is a thermoplastic crystalline polymer; (4) the polymer is a thermoplastic crystalline polymer of aromatic diamines and aromatic dicarboxylic anhydrides; (5) the polymer is a glass-fiber reinforced polyarylamide; (6) the polymer is at least 50% glass-fiber reinforced; (7) the polymer has a flexural modulus of at least 17 Gpa; (8) the polymer has a flexural strength of at least 375 Mpa; (9) the polymer has an impact strength of at least 100 J/M; (10) the illumination assembly is permanently attached to the curved portion; and/or (11) the polymer has a conductivity of less than 10-6 A.

Further features and advantages will be apparent to those skilled in the art after reviewing the drawings and detailed description provided herein.

BRIEF DESCRIPTION OF THE DRAWINGS

FIGS. 35A-35B are internal views of the end cap assembly of FIG. 34 including a battery assembly and an activation switch.

FIGS. 36A-36B are views of a portion of the end cap assembly of FIG. 34 showing alignment between the battery assembly, the activation switch and a releasable battery door;

DETAILED DESCRIPTION OF SELECT EXEMPLARY EMBODIMENTS

Figure 1:
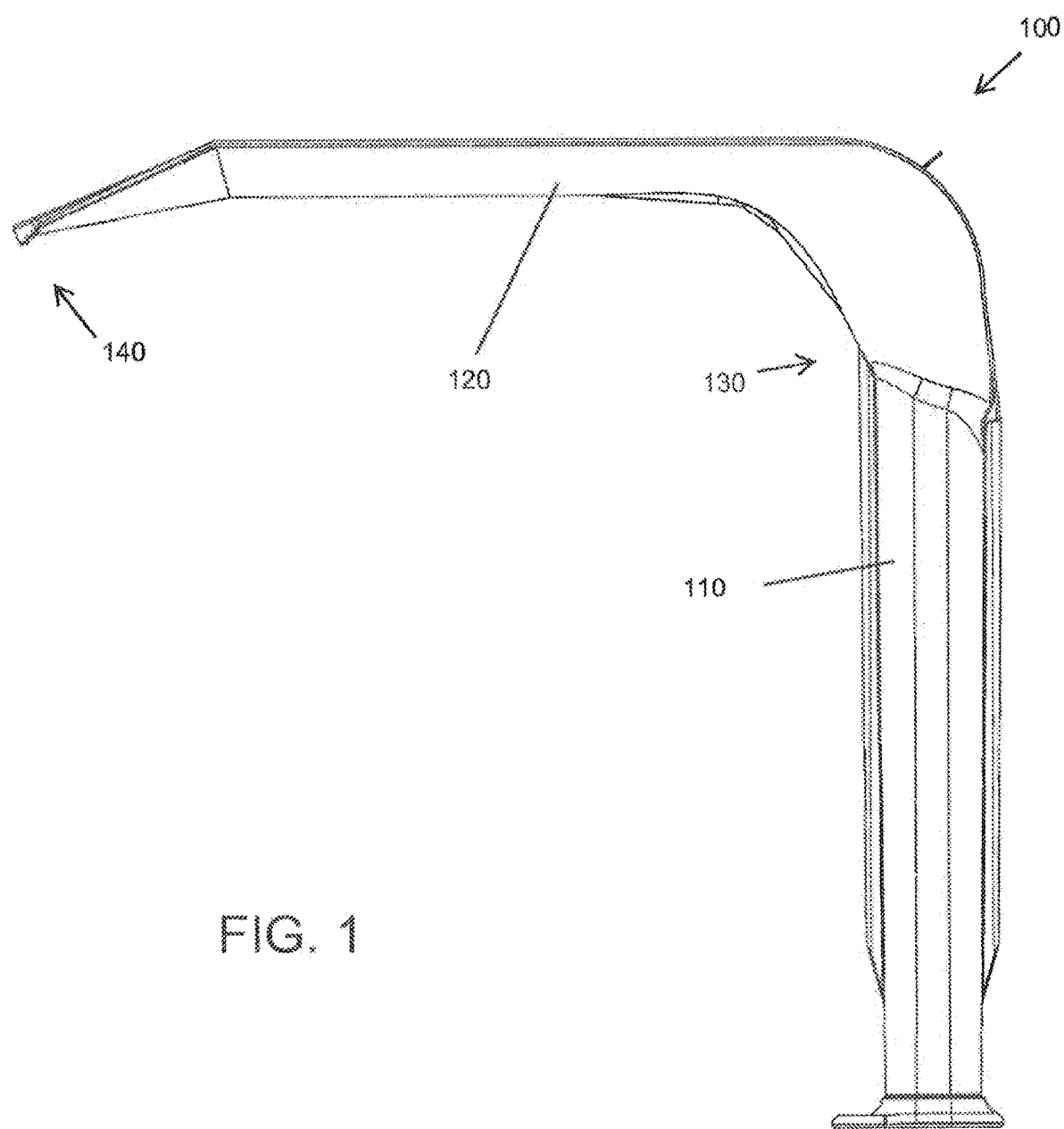
FIG. 1 is a side view of an exemplary embodiment.

The following detailed description is of certain exemplary embodiments. The description is not to be taken in a limiting sense, but is made merely for the purpose of illustrating the general principles of the present retractor.

Broadly, one or more embodiments provide a surgical retractor including an integrated light source and rounded blade forming an unobstructed, illuminated viewing slot for the physician's field of view. The surgical retractor with integrated light source prevents the problem caused by external light sources—namely, the casting of shadows within the operating cavity. To solve this problem, the integral light source of the surgical retractor is pointed in the same direction as the distal end of the retractor, which causes the light to be directed to the same point where the cutting is being performed.

The surgical retractor may provide a handle portion generally perpendicularly joined to a blade portion. The blade portion may form an arcuate (curved) shaped barrel portion defining a viewing slot, wherein the blade portion interconnects a saddle portion and an operative portion. The operative portion is dimensioned and adapted for surgery. The saddle portion attaches to the handle portion, while forming a recessed cavity for receiving the light source. The light source and recessed cavity are disposed, dimensioned, and adapted so that the light beam from the light source is directed down the viewing slot.

Referring now to FIGS. 1 through 22, one or more exemplary embodiments may include a surgical retractor 100 integrated with a light assembly 205. The surgical retractor 100 may include a handle portion 110 generally perpendicularly joined to a blade portion 120. The handle portion 110 may be joined to the blade portion 120 at saddle portion 210. The blade portion 120 may extend from a proximal end 130 to a distal end 140, wherein the proximal end 130 is joined to the handle portion 110 at saddle portion 210.

The blade portion 120 may be made of any moldable material that is sufficiently resilient including, but not limited to, polystyrene, poly-carbonate, glass filled nylon, or the like, although as explained herein, glass-reinforced polyarylamide is preferred, due its superior strength, radiolucency, and low conductivity.

The blade portion 120 may form a saddle portion 210, a barrel portion 215, and an operative portion 220.

The blade portion 120 may extend from the proximal end 130 to the distal end 140, wherein the barrel portion 215 interconnects the saddle portion 210 and the operative portion 220.

The barrel portion 215 may form an arcuate shape along its length so that the trough of the arcuate shape is upwardly oriented, defining a "viewing slot," as illustrated in the drawings.

The saddle portion 210 may be formed in a bowl-like configuration. The saddle portion 210 may form a recessed cavity 605 for receiving the light assembly 205. A spring or other fastener (not shown) may be provided to secure the light assembly 205 in the recessed cavity 605.

The light assembly 205 may include a light source 305, a switch 310 and a power source 315 connected in series. The power source 315 may include batteries, such as button style batteries, adapted to store only sufficient energy for a single use. Alternatively, the batteries may be reusable or rechargeable batteries for multiple uses. The light source 305 may be enclosed by a housing 320. The light source may include a LED, OLED, incandescent, or other suitable light source for emitting a beam of light. The switch 310 may be a light tab made from a nonconductive material, such as a Mylar tape, adapted to open circuit the serial electrical circuit of the power source 315 and the light source 305, whereby removal of the switch 310 results in the power source 315 activating the light source 305. In certain embodiments, the switch 310 may utilize any known means of activating/powering the light source 305, such as, but not limited to, a push button switch, toggle switch, magnetic reed switch or slider switch.

Figure 2:
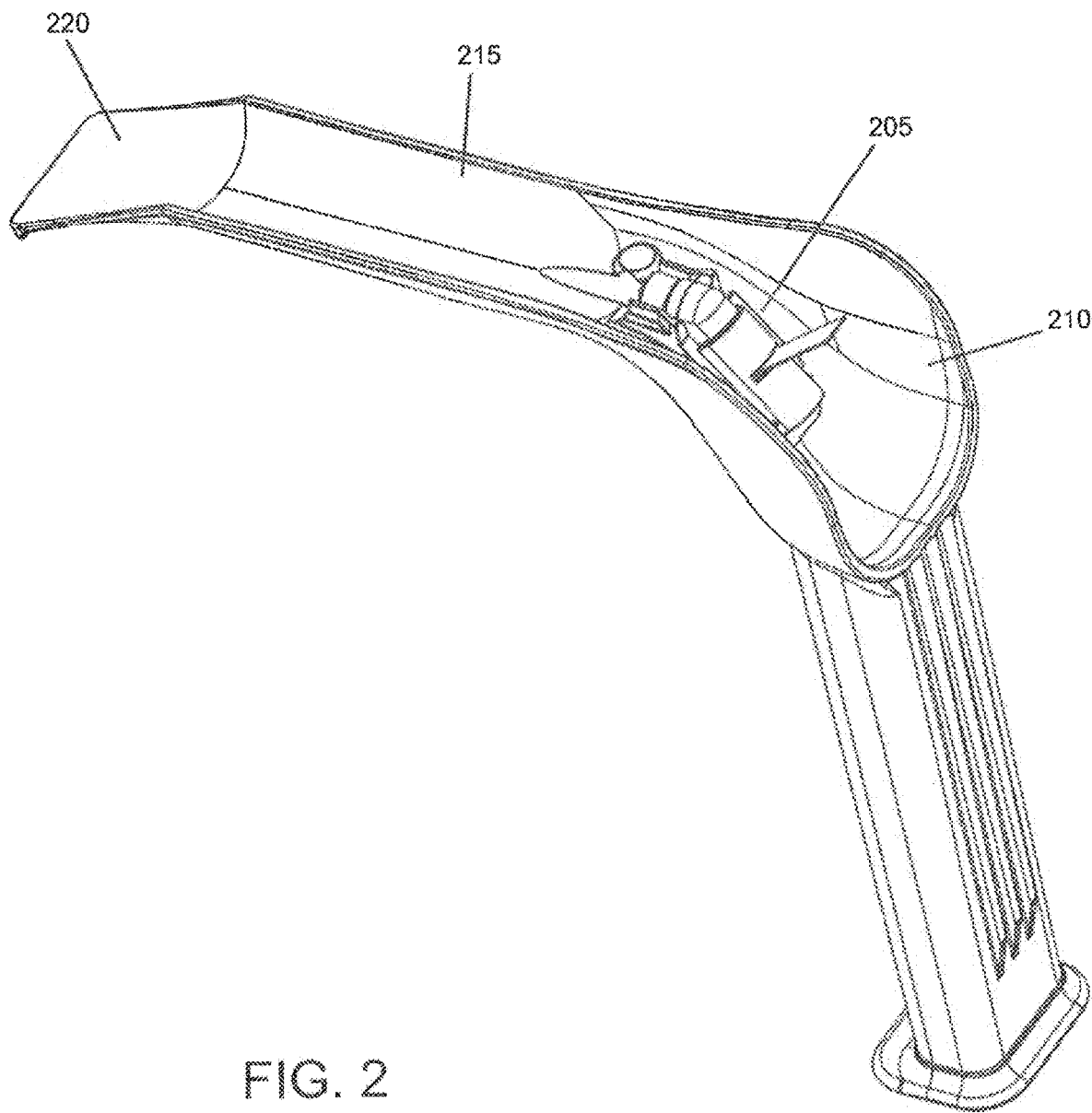
FIG. 2 is a diametric view of an exemplary embodiment.
Figure 3:
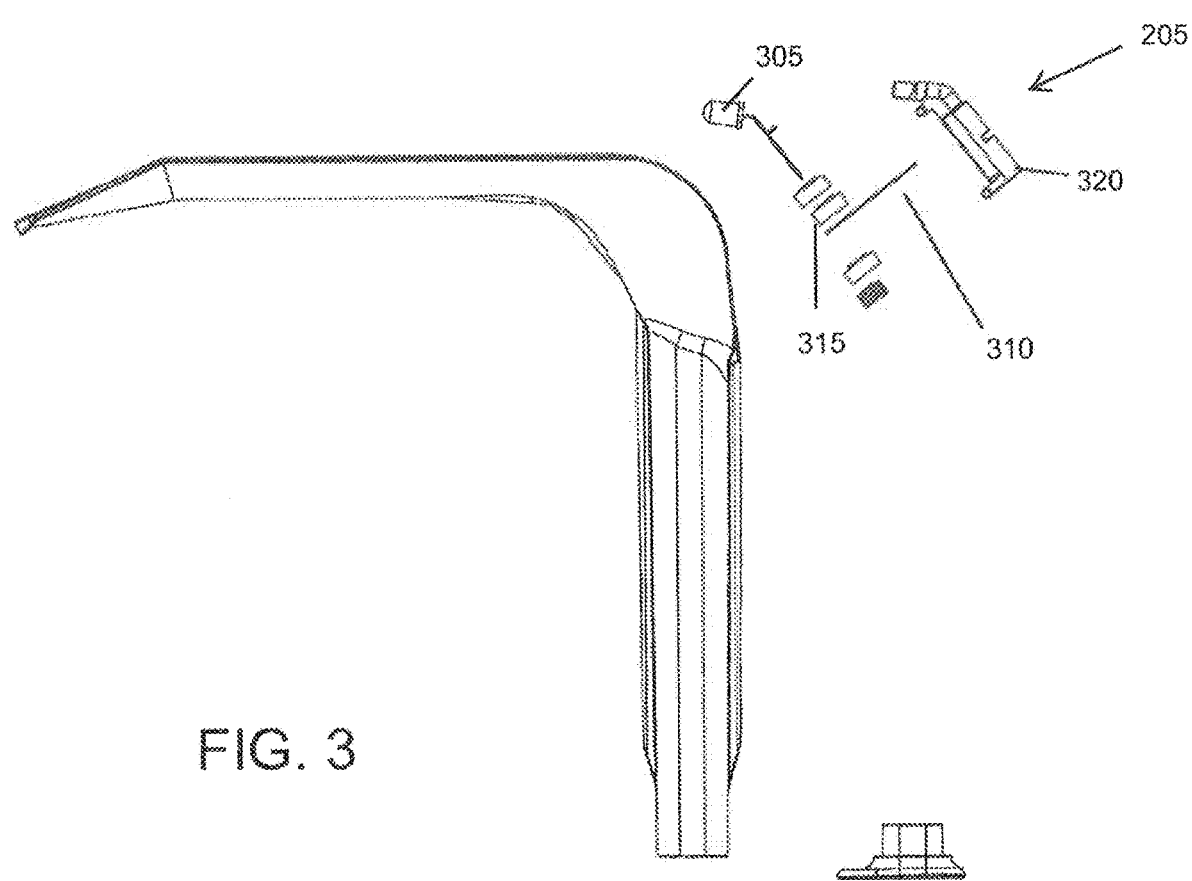
FIG. 3 is an exploded view of an exemplary embodiment.
Figure 4:
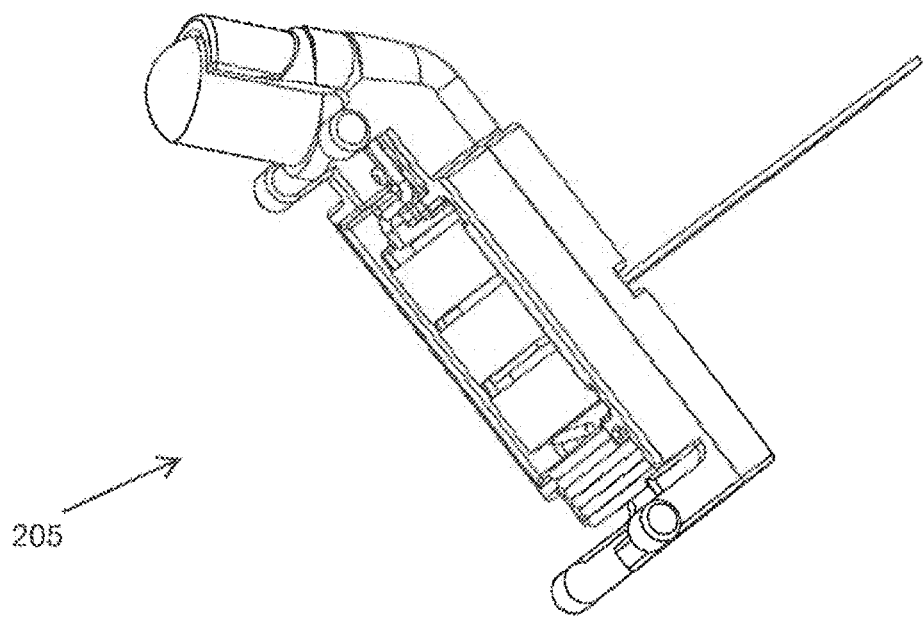
FIG. 4 is a perspective view of an exemplary embodiment.
Figure 5:
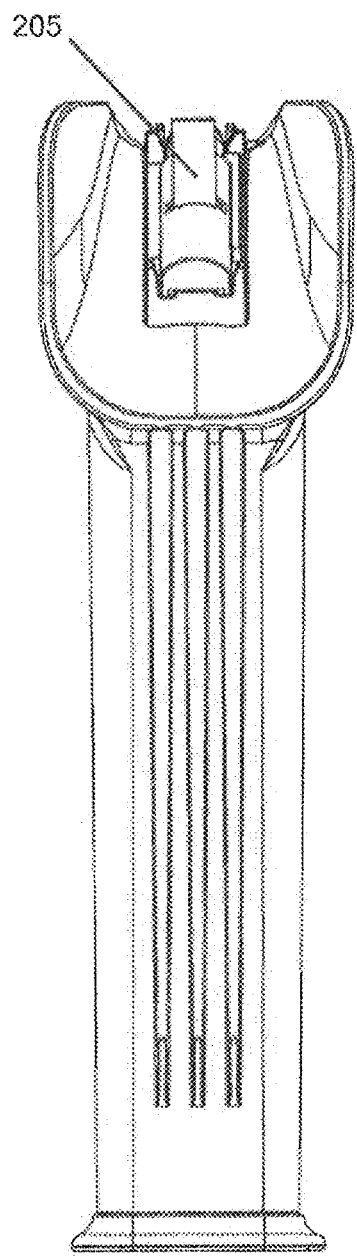
FIG. 5 is a rear view of an exemplary embodiment.
Figure 6:
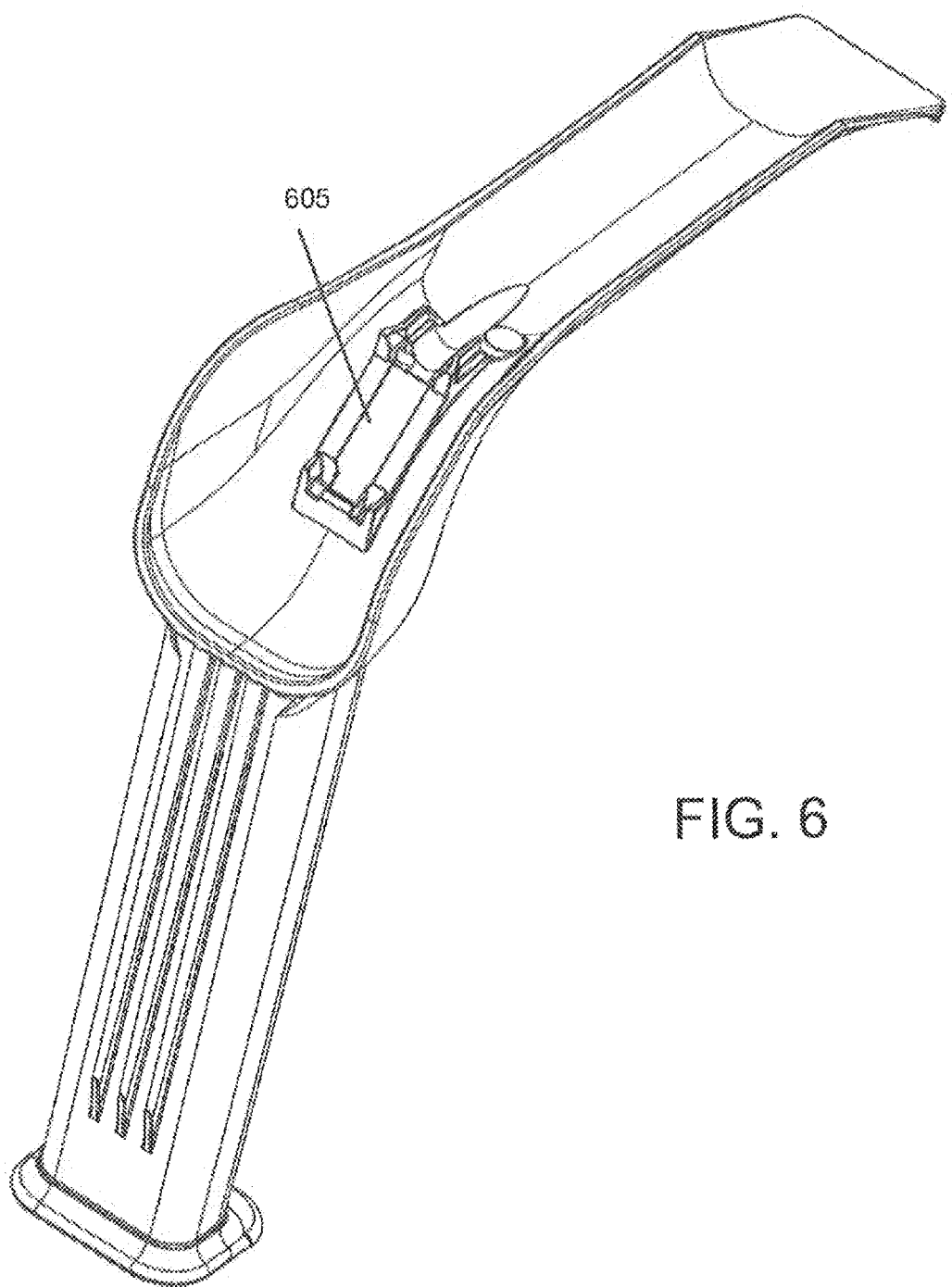
FIG. 6 is a perspective view of an exemplary embodiment, with the light assembly removed for clarity.
Figure 7:
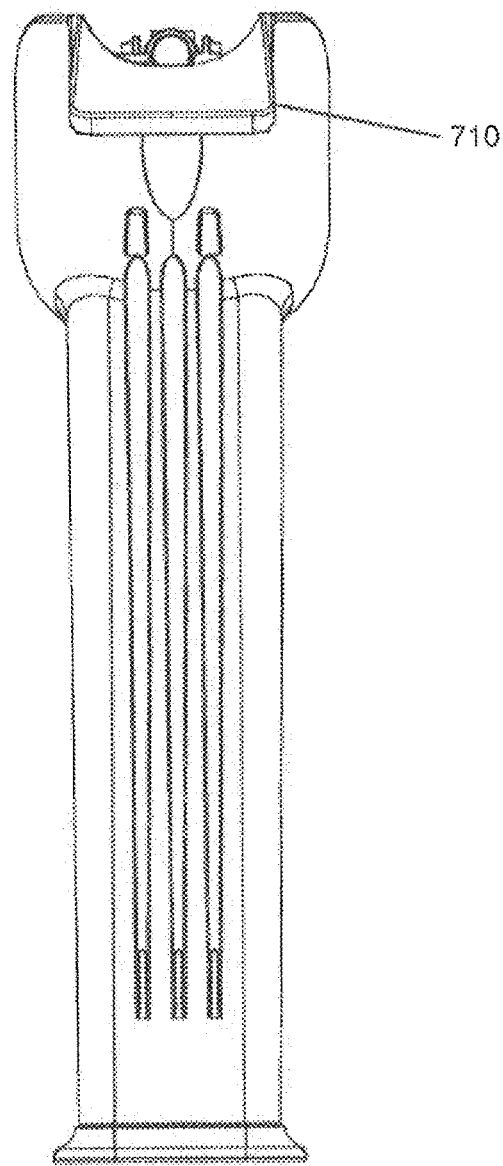
FIG. 7 is a front view of an exemplary embodiment.
Figure 8:
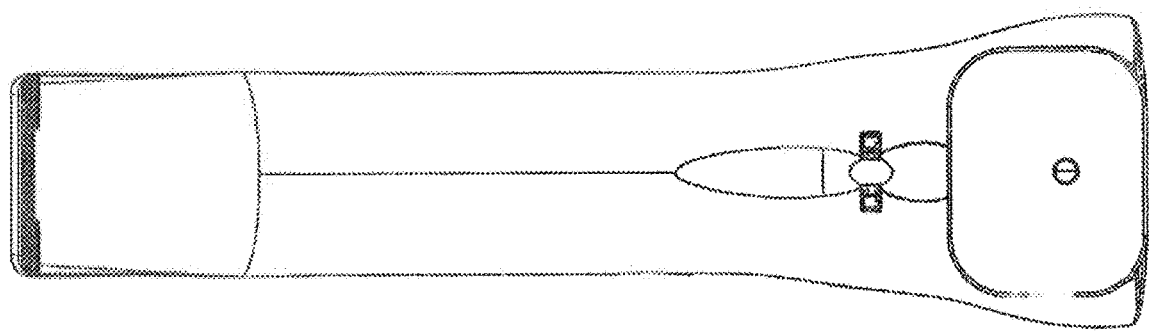
FIG. 8 is a top view of an exemplary embodiment.
Figure 9:
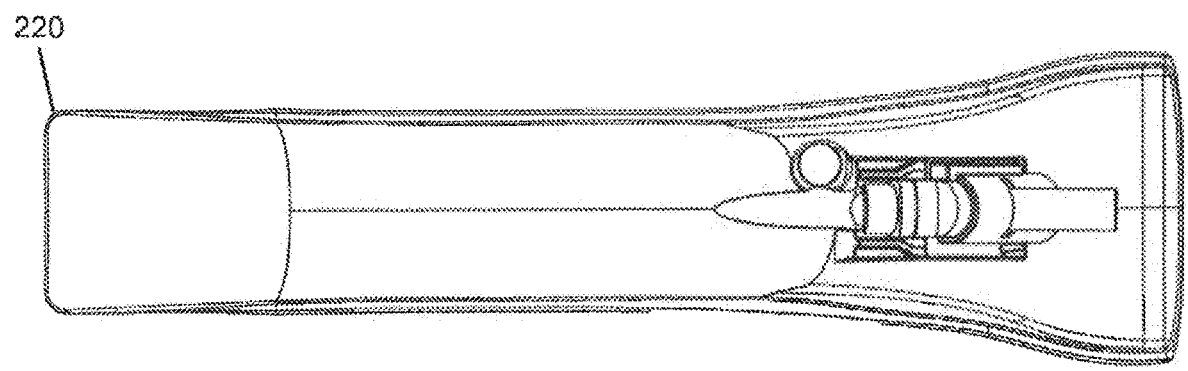
FIG. 9 is a bottom view of an exemplary embodiment.

The recessed cavity 605 and the light source 305 may be dimensioned and adapted so that the beam of light is directed along the viewing slot, toward the distal end 140 of the blade portion 120, as illustrated in FIGS. 2 and 6, which illustrate the light source 305 disposed in the saddle portion 210 and directed down the viewing slot of barrel portion 215. As shown, the housing 320 is disposed below the viewing slot, and therefore out of the field of view of the end user.

The operative portion 220 may be downwardly angled away from the viewing slot so as to not obstruct the above-mentioned field of view. The operative portion 220 may be substantially flat and/or substantially square or rectangular in shape, providing a distal tip with a plurality of ridges 710 opposite the barrel portion 215. The shape of the distal tip and the ridges 710 may be dimensioned and adapted to hold the tissue of the breast recessed cavity away from the area of dissection, which helps the end user in the dissection procedure. Ridges 710 may be of any suitable depth and size in order to hold the breast tissue.

A method of using the retractor may include the following. The surgical retractor 100 disclosed above may be provided. A user may remove the surgical retractor 100 from a sterile package just prior to the surgical procedure. The user may remove the switch 310 to energize the light source 305. The user may then create an incision in the patient and use the surgical retractor 100 to create a pocket through this incision. The pocket will be used for breast augmentation, reconstruction, or other breast related surgical procedures. When the procedure is over, the retractor 100 may be discarded, because the light source 305 may be designed to not be replaceable and the power source may only be sufficient to power the light source for a single procedure, thereby allowing disposal of the present embodiment after one use.

In certain embodiments, the surgical retractor 100 can be adapted to form a retractor suitable for other procedures such as a nasal retractor spine retractor, orthopedic retractor, and retractors for other surgical procedures. All such retractors maintain the present embodiment of fully assembled, lighted, and single use.

In certain embodiments, the retractor may be used in a medical procedure performed by robots. Such robots will also need lighted retractors to allow visualization of the surgical cavity. Robotic procedures also benefit from enhanced field of view, and from single use components that eliminate the risk of patient cross contamination. An embodiment will contain suitable connecting features for attachment to a medical robot.

FIGS. 10-22 depict embodiments comprising a retractor 100 with a light source 1020 located toward or near the distal end 140 of the barrel portion 215. It should be noted that some or all of the features as discussed herein with reference to these embodiment may be used in conjunction with, or in place of, some or all of the features in embodiments previously disclosed.

Referring now to FIGS. 10-20, retractor 100 may include a light source 1020 located nearer to the operative portion 220. The light source 1020 may be located toward the distal end of barrel portion 215. Light source 1020 may be located at any point near the distal end 140, including within the barrel portion 215 and the operative portion 220.

Light source 1020 may include a wide dispersion angle, such as a 100 degree angle, or any suitable variation thereof. The wide dispersion angle may be attained by using a wide dispersion LED. The use of light source 1020, with a wide dispersion angle, and its location toward the distal end 140 of the blade portion, provides light to the entire operative area located in front of operative portion 220.

Figure 10:
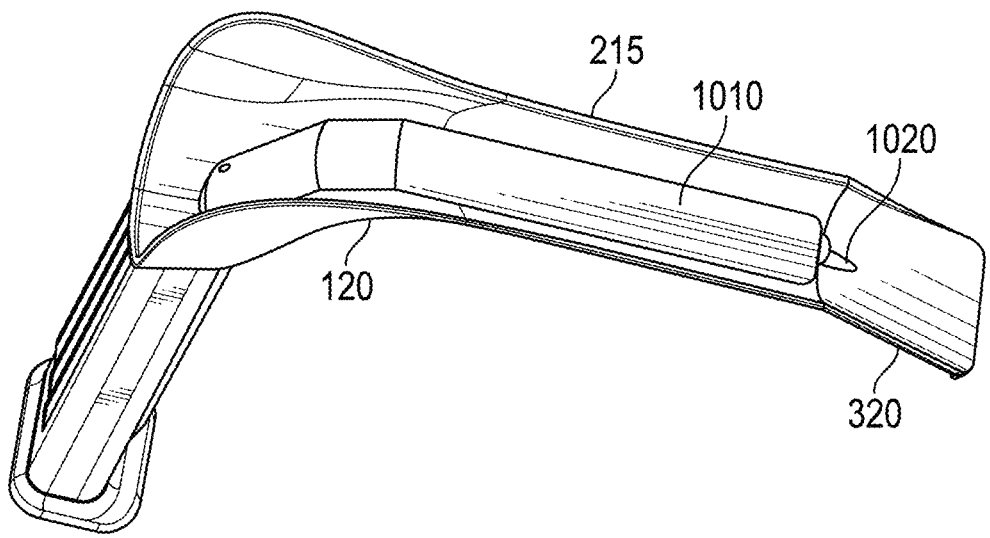
FIG. 10 is a top view of an exemplary embodiment.

As illustrated in FIG. 10, the light source 1020 may be associated with some or all of the features of light assembly 205, including light source 305, a switch 310 and a power source 315.

Figure 13:
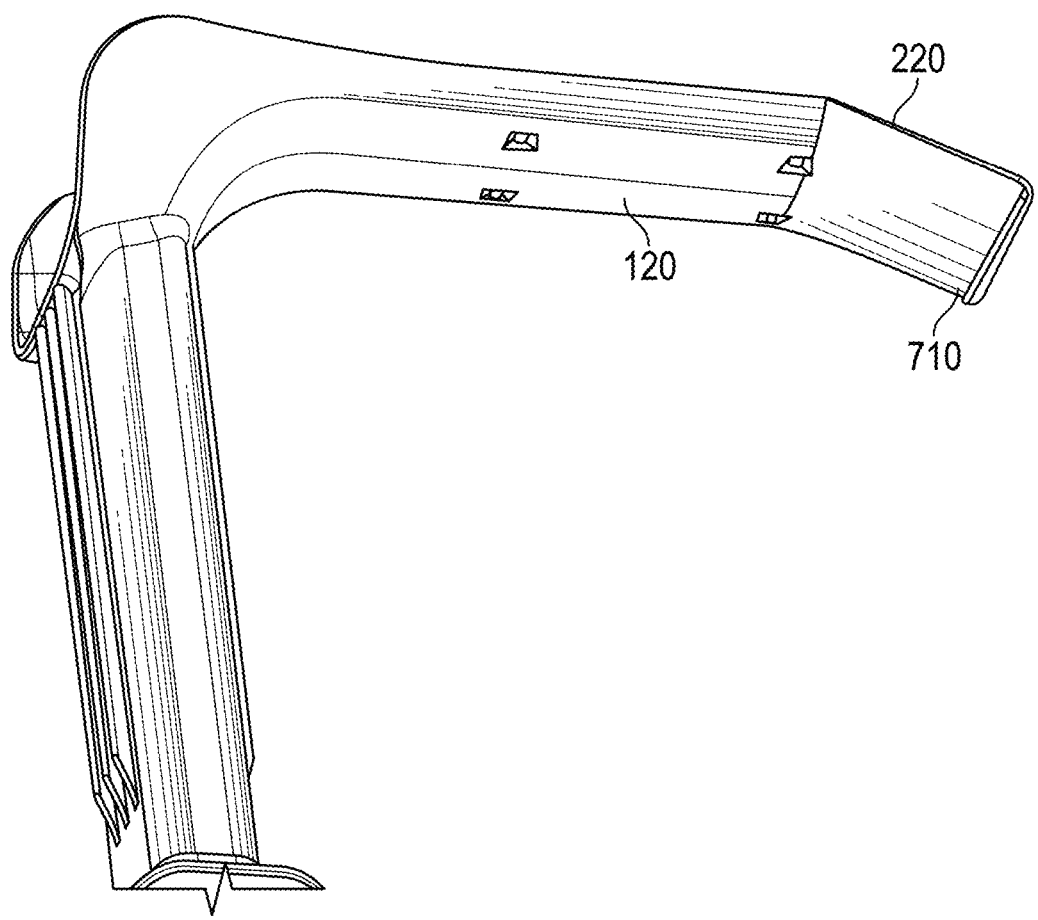
FIG. 13 is a side perspective view of an exemplary embodiment.

Further, in this embodiment, operative portion 220 may include integral ridges 710, shown in FIG. 13, which provide for holding back tissue during use of the retractor 100.

A smoke evacuation channel 1105, with channel cover 1010, is located within barrel portion 215, and may extend, at one end, up to operative portion 220. In some embodiments, the smoke evacuation channel 1105 and cover 1010 may extend into a portion of the operative portion 220 at one end. The channel 1105 may be a hollow cavity defining the barrel portion 215.

At a second end, the smoke evacuation channel cover 1010 may be anchored in the saddle portion 210. The smoke evacuation channel 1105 may then extend into a hollow space located within handle 110. Thus, handle 110 may include a hollow space for receiving the smoke evacuation channel 1105 and cover 1010.

As illustrated, the smoke evacuation channel cover 1010 may be angled at certain points. The smoke evacuation channel 1105 may also incorporate light source 1020. Light source 1020 may further include a light holder 1115.

Channel 1105, coupled with cover 1010, provided for air and smoke to enter channel 1105 via a gap between cover 1010 and the barrel portion 215, thereby guiding smoke away from the physician's field of view. The gap may be provided on either side of the light source 1020.

Figure 14:
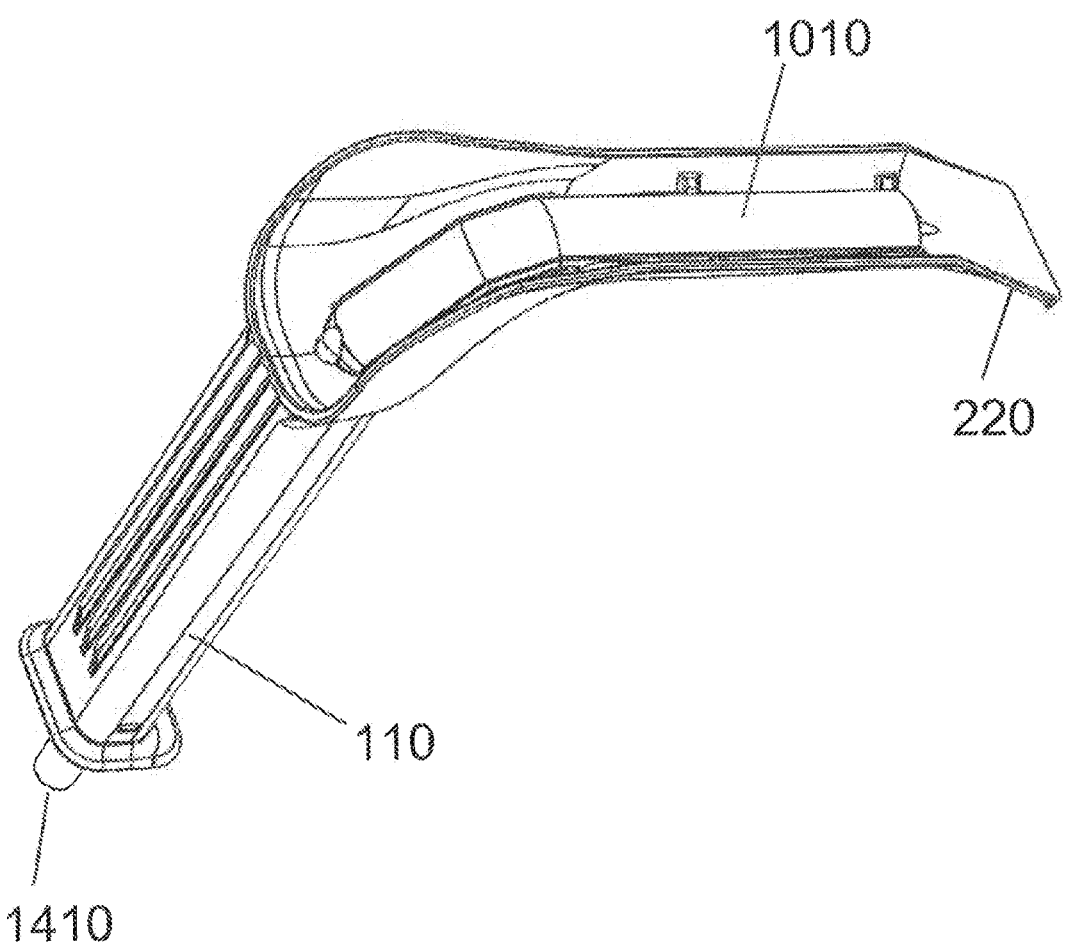
FIG. 14 is a top perspective view of an exemplary embodiment.

The smoke channel 1105 and cover 1010 may extend from the distal end 140 of the retractor 100, near the operative portion 220, towards handle 110, as shown in FIG. 14.

Channel 1105 conducts air or smoke received at the entrance of the channel 1105, located at the distal end of the blade portion 120, towards the handle portion 110. Channel 1105 therefore acts as an air conduit and moves air/smoke away from the incision site and/or the physician's field of view.

A vacuum source may be attached to the retractor 100. The vacuum source may be connected to any point of the handle portion 110, including the bottom of the handle 110, distal to the saddle portion. Alternatively, the vacuum source may be attached at any suitable location to the handle portion 110, or may be attached directly to the cover 1010 at the location of the saddle portion 210.

The handle portion 110 may be hollow and act as an air conduit. Smoke or air may leave the channel 1105 at the entrance to the handle portion 110, which may include a hollow chamber that is in communication with channel 1105. The handle portion 110 may include a portion of channel 1105, which is integral with the other portion of cover 1010. Alternatively, the handle portion 110 may include a second cover in communication with channel 1105, and may receive the smoke/air from channel 1105. The vacuum source may be attached at the base of the handle portion 110.

The vacuum source is operable to provide suction, via the channel 1105, in order to move air/smoke away from an incision site or the physician's field of view. The air/smoke enters the channel 1105 at an opening created by the gap between cover 1010 and barrel portion 215, located near the blade tip, traverses the channel 1105 toward the saddle portion 210, and enters the handle portion 110. The vacuum source pulls the air/smoke from the handle.

Figure 15:
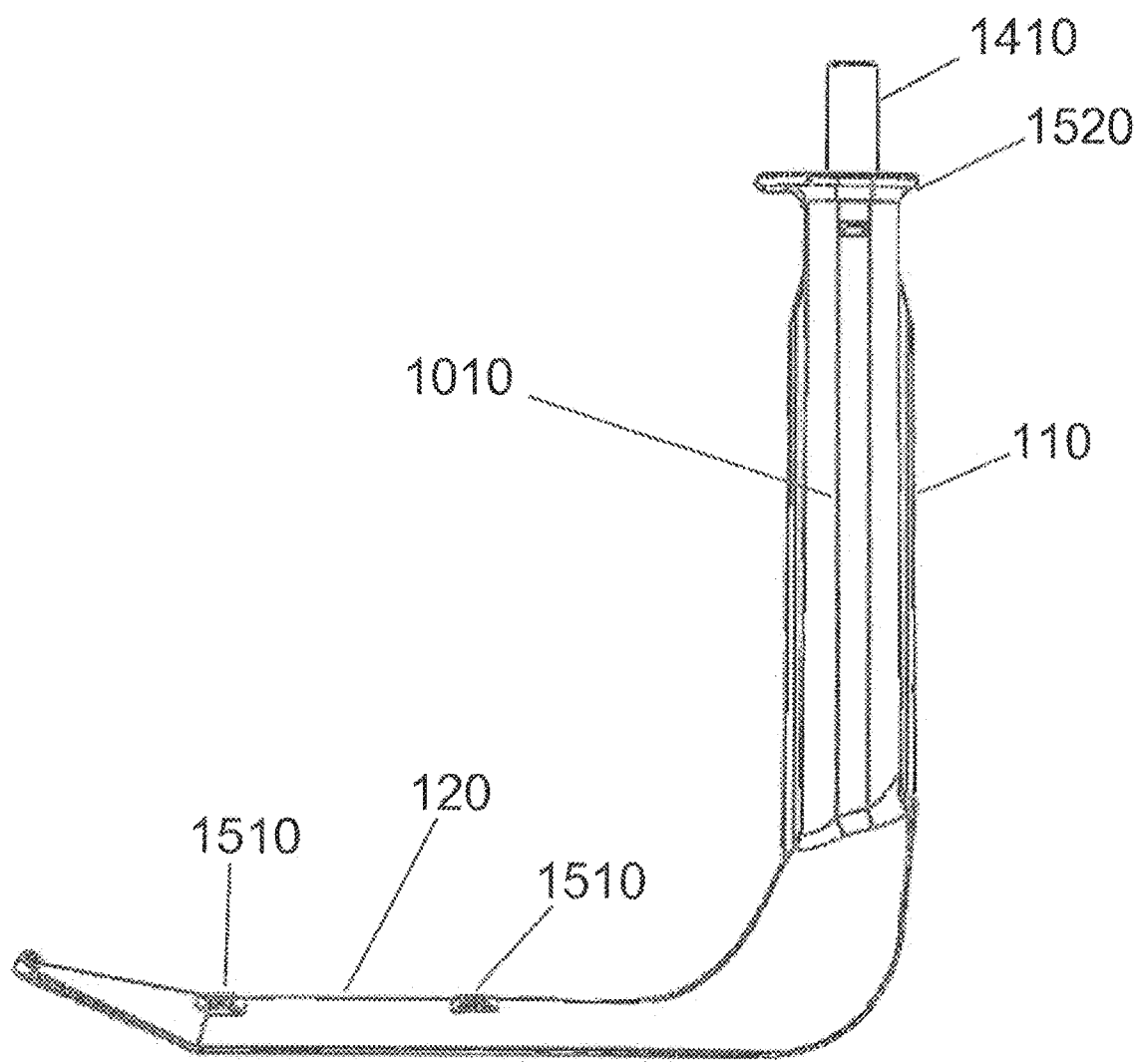
FIG. 15 is an inverted view of an exemplary embodiment.

As illustrated in the inverted view of the retractor 100 in FIG. 15, the channel 1105 and cover 1010 descend to the bottom 1520 of the handle portion 110. The cover 1010 includes a connector 1410 at the bottom 1520, which fluidly connects the channel 1105 to the vacuum source and draws the smoke/air out of the channel.

Figure 11:
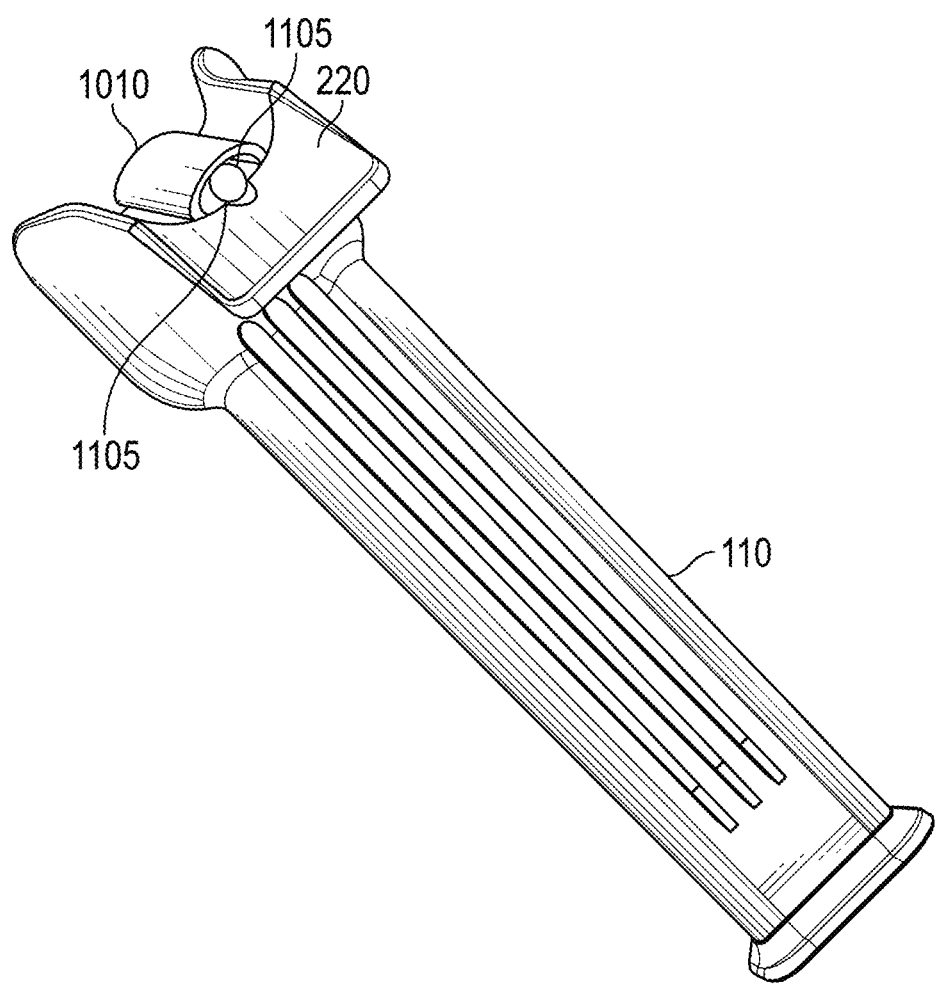
FIG. 11 is a front angled view of an exemplary embodiment.
Figure 12:
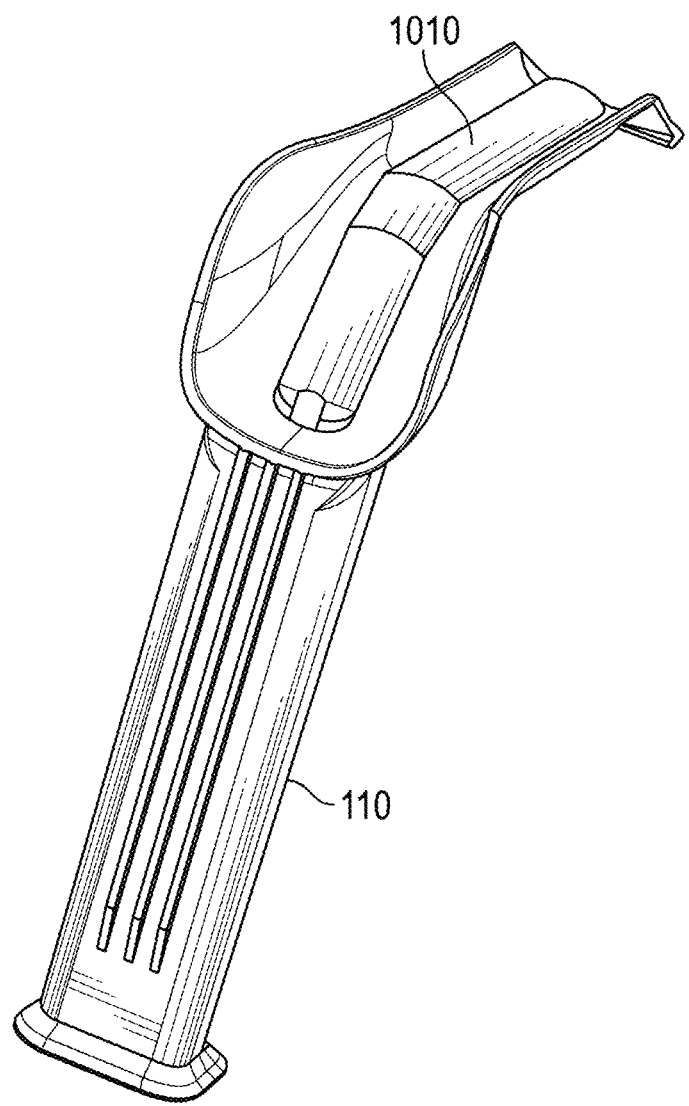
FIG. 12 is a rear view of an exemplary embodiment.

As illustrated in FIGS. 11-13, the smoke channel 1105 advantageously abuts operative portion 220 in order to provide smoke evacuation from the operative site. Further, the light source 1020 may be provided at an angle similar to, or substantially the same as, the downward angle of the operative portion 220 relative to the barrel portion 215, in order to focus the light from the light source 1020 onto the area retracted by the operative portion 220.

The light source 1020 may alternatively be provided at an angle substantially similar to the barrel portion 215, and may not slope downward with the operative portion 220. This may still cause the light source to illuminate the operative area, due to the wide dispersion angle of the light source 1020.

Yet further illustrated is the angle of the operative portion 220, particularly at the distal end as it slopes downward. Integral ridges 710 provide, along with the angle of the blade 120 at its operative portion 220 and the square shape of the operative portion 220, for optimal methods and apparatus for holding back tissue during use.

Figure 17:
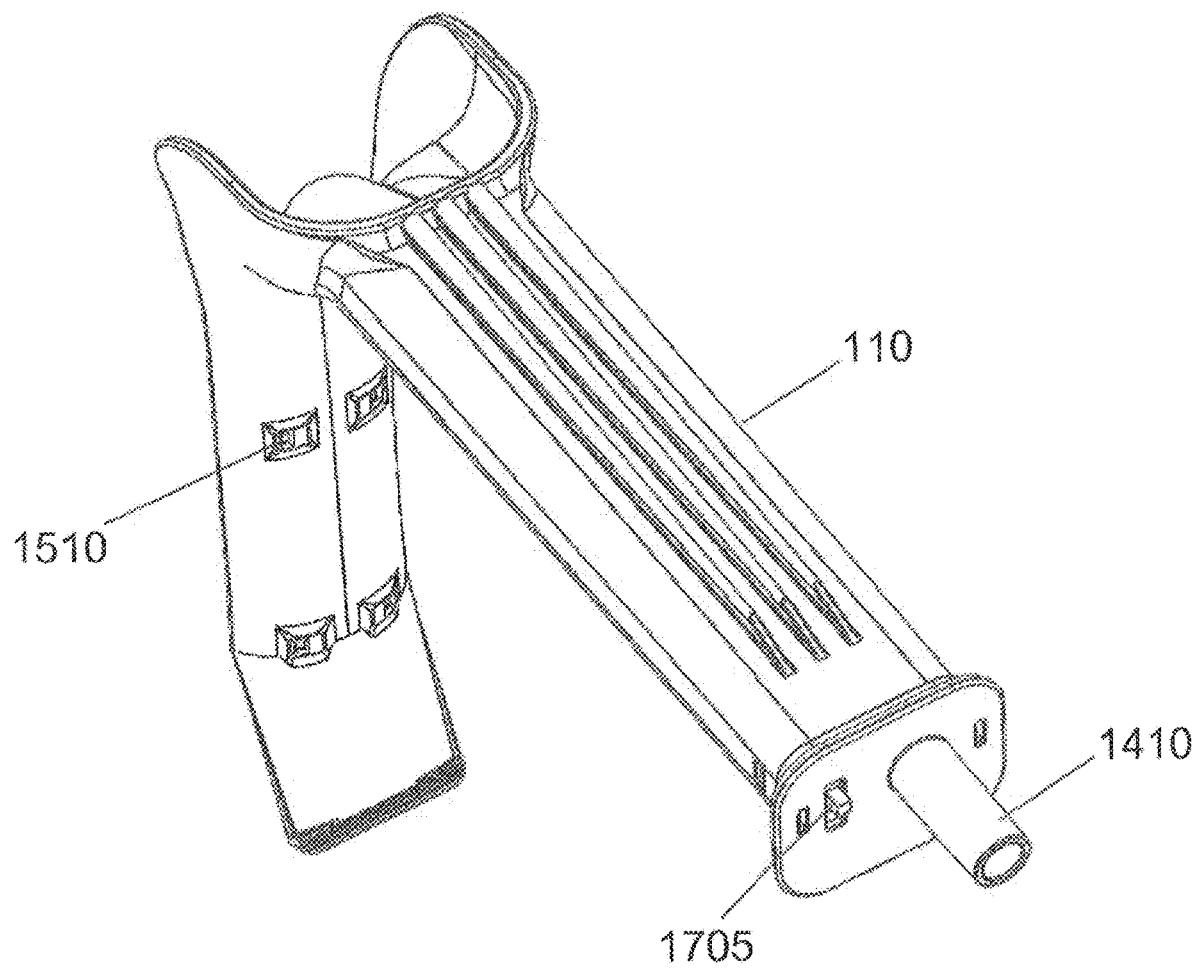
FIG. 17 is a rear perspective view of an exemplary embodiment.

Blade 120 may incorporate one or more retaining slots 1510, shown in FIGS. 15 and 17, on the underside of the blade. The slots 1510 are operable to hold cover 1010 in place. The retaining slots 1510 are also optimally designed to not catch tissue during a surgical procedure, such as when the blade 120 is inserted into the body cavity.

Figure 16:
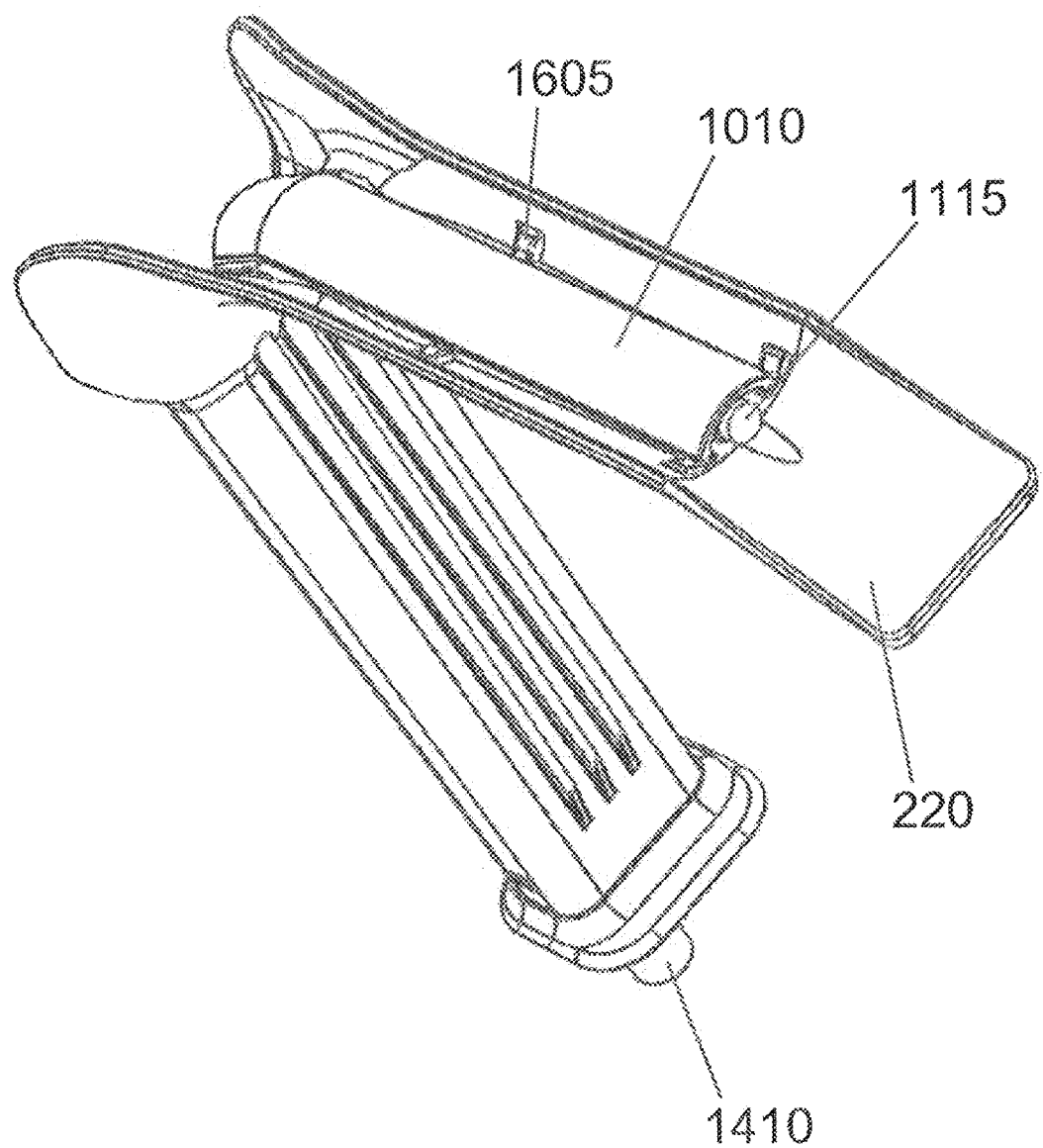
FIG. 16 is a side perspective view of an exemplary embodiment.

Each retaining slot 1510 incorporates a hole sized to receive a retaining tab 1605 from cover 1010, as shown in FIG. 16. To hold cover 1010 in place on top of blade 120, the retaining tab 1605 from cover 1010 is inserted into the hole of retaining slot 1510. Retaining slots 1510 are sized such that the hole is smaller than the associated retaining tab 1605. The hole is raised and smoothed, which holds body tissue away from the hole.

Figure 21:
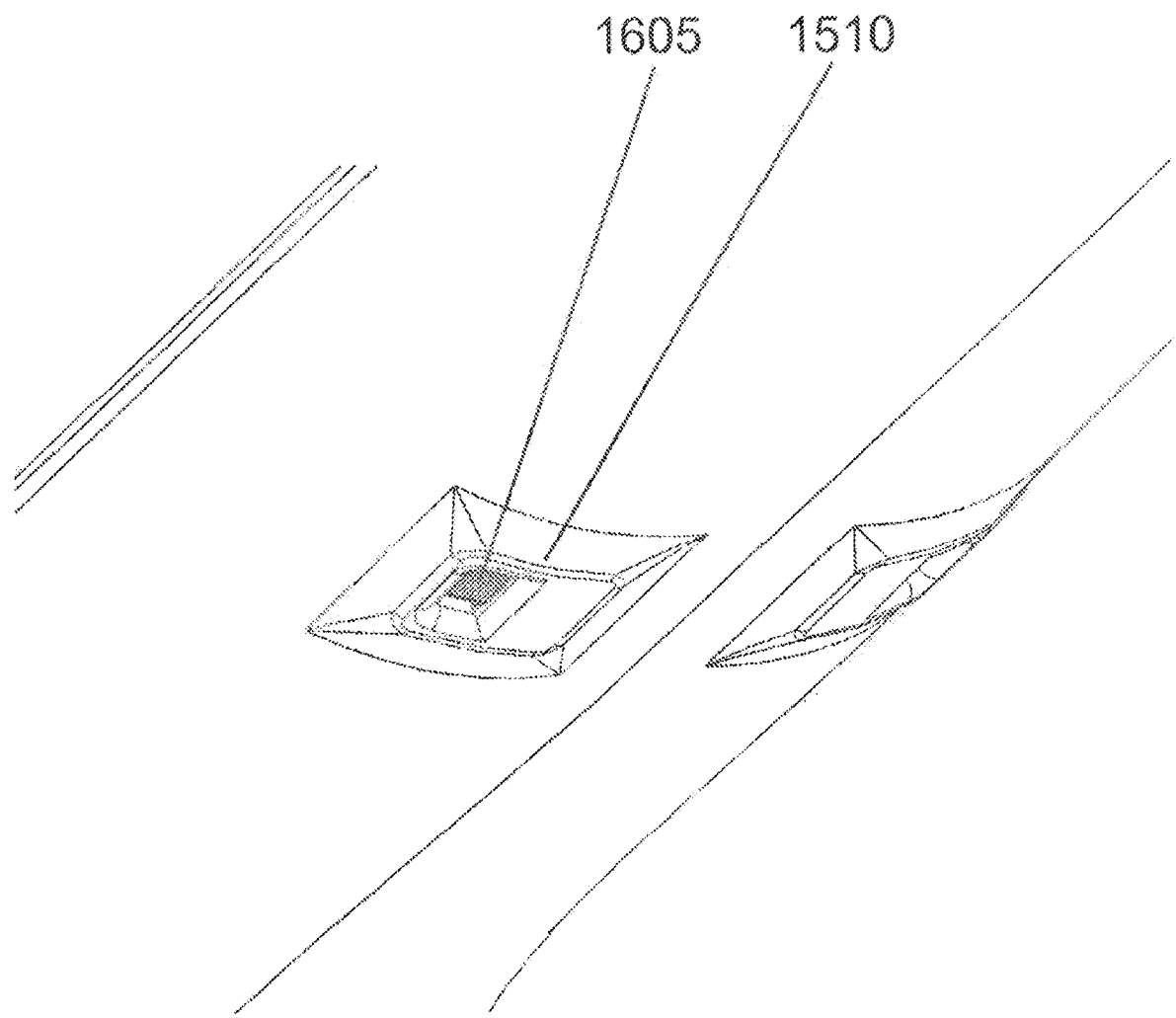
FIG. 21 is a view of an exemplary embodiment.

As illustrated in FIG. 21, retaining slot 1510 may include a raised and smoothed portion. Based on this feature, the retaining tab 1605, when inserted into and residing within retaining slot 1510, is recessed within the hole, and does not protrude from the hole of retaining slot 1510. This ensures that no tissue is snagged or caught by the end of retaining tab 1605.

Figure 22:
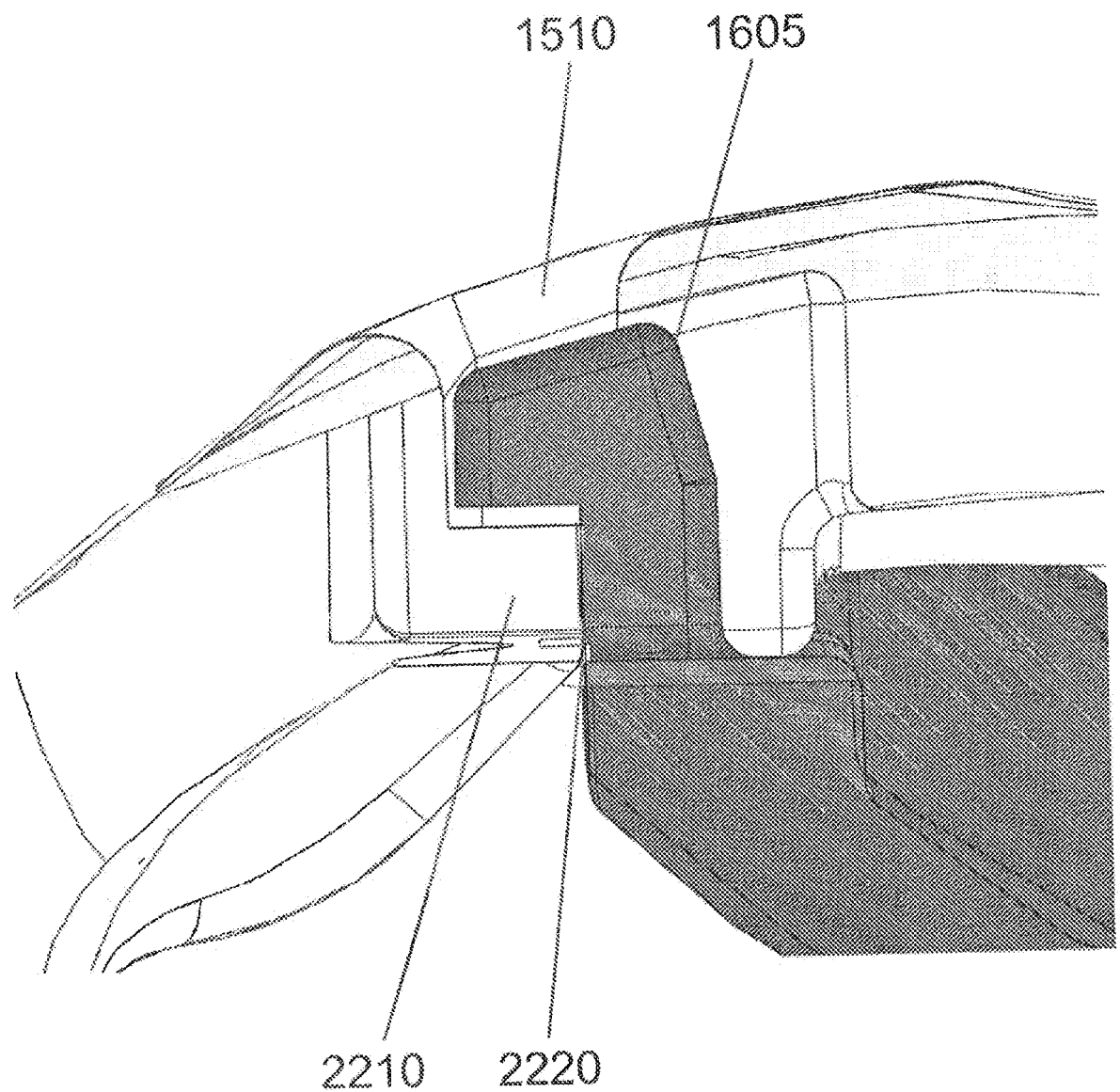
FIG. 22 is another view of an exemplary embodiment.

FIG. 22 illustrates a cutaway of tab 1605 residing within, and not protruding from, retaining slot 1510. Tab 1605 deforms around shelf 2210, and tab 1605 snaps into place such that contact between the underside of tab 1605 and the top of shelf 2210 prevents the separation of tab 1605 from shelf 2210.

Shelf 2210 is located opposite retaining slot 1510. Retaining slot 1510 is located on the underside of blade portion 120, and is formed from mold structures that penetrate the blade portion 120 from the underside. The penetration of the mold structures forms holes in the blade portion 120, such as retaining slot 1510, which is shown filled in with tab 1605. To prevent retaining slot 1510 from trapping tissue, it is preferable to minimize the size of retaining slot 1510, as well as limit the number of holes to one hole located on the underside of blade portion 120.

Retractor 100 is therefore formed using a mold structure that penetrates blade portion 120 only in the location of shelf 2210. The formed hole of retaining slot 1510 is minimized in size to be of the same, or approximately the same, size as the width of shelf 2210.

In an embodiment, the manufacturing process includes utilizing the mold structures to form a hole in the underside of the blade portion (e.g., in the hole of retaining slot 1510), opposite shelf 2210. By penetrating the blade portion 120 only in the location of the shelf, and in no other location on the underside of the blade portion, the hole on the underside, which may face the patient during a procedure, is only as wide as the shelf. Thus, the hole size is reducing trapping of patient tissue.

Yet, by reducing the hole area for retaining slot 1510, and providing for one hole the same width of shelf 2210, during manufacturing, retaining tab 1605 cannot deform into place to fit around shelf 2210.

As illustrated in FIG. 22, an additional hole 2220 is therefore formed during manufacturing from a mold structure on the top side of blade portion 120, opposite the tissue-facing underside, in order to allow for deformation of retaining tab 1605.

Hole 2220 is formed to provide for deformation of retaining 1605. The location of hole 2220 is optimally located on the top side of blade portion 120, away from tissue contact. Hole 2220 does not proceed through the width of the blade portion 120, thereby minimizing additional hole structures on the patient-facing side of retractor 100.

As illustrated in FIGS. 21-22, retaining slot 1510, is sized to half the width of a conventional hole, due to the use of multiple molds. Therefore, only slot 1510, with a smoothed mound, provides for minimal tissue catch.

In an embodiment, the retractor 100 is formed from an injection mold design. It should be noted that a shrunken hole is smaller than the retaining tab 1605, which is only possible in an injection mold design, and is not feasible with a metal retractor.

Retractor 100 further includes an on/off switch 1705, located at the bottom of handle 110. Switch 1705 may be located adjacent to the connector 1410. Switch 1705 controls one or more of the light source and vacuum source.

Figure 18:
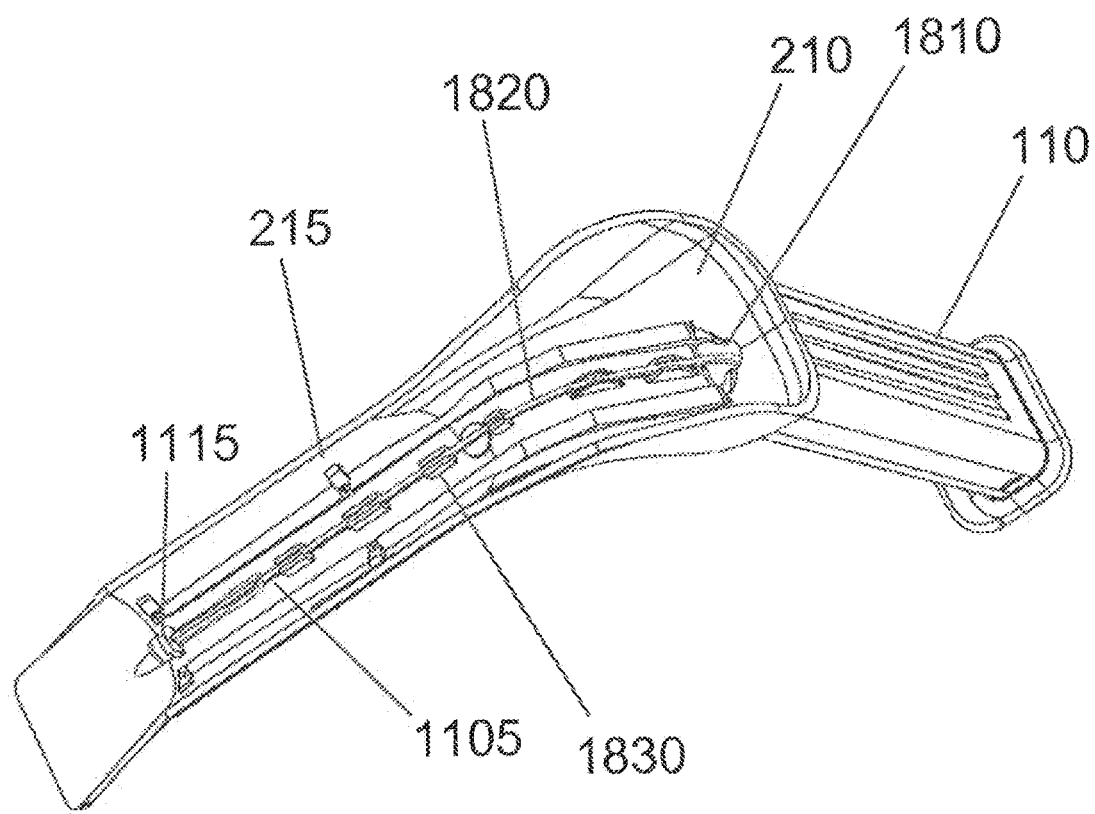
FIG. 18 is a top perspective view of an exemplary embodiment.

FIG. 18 illustrates the retractor 100 with cover 1010 removed. Channel 1105, the cavity, under the smoke evacuation cover 1010, is illustrated extending from a distal end of the barrel portion 215 adjacent to the operative portion 220, past the saddle portion 210, and into a cavity 1810 located in the handle 110. Smoke may travel from the intake adjacent to operative portion 220, under the cover 1010, via channel 1105, into the handle cavity 1810. The smoke traverses the internal cavity 1810 and exits the handle via connector 1410, which is connected to a smoke evacuation hose and uses suction from the vacuum source.

Figure 19:
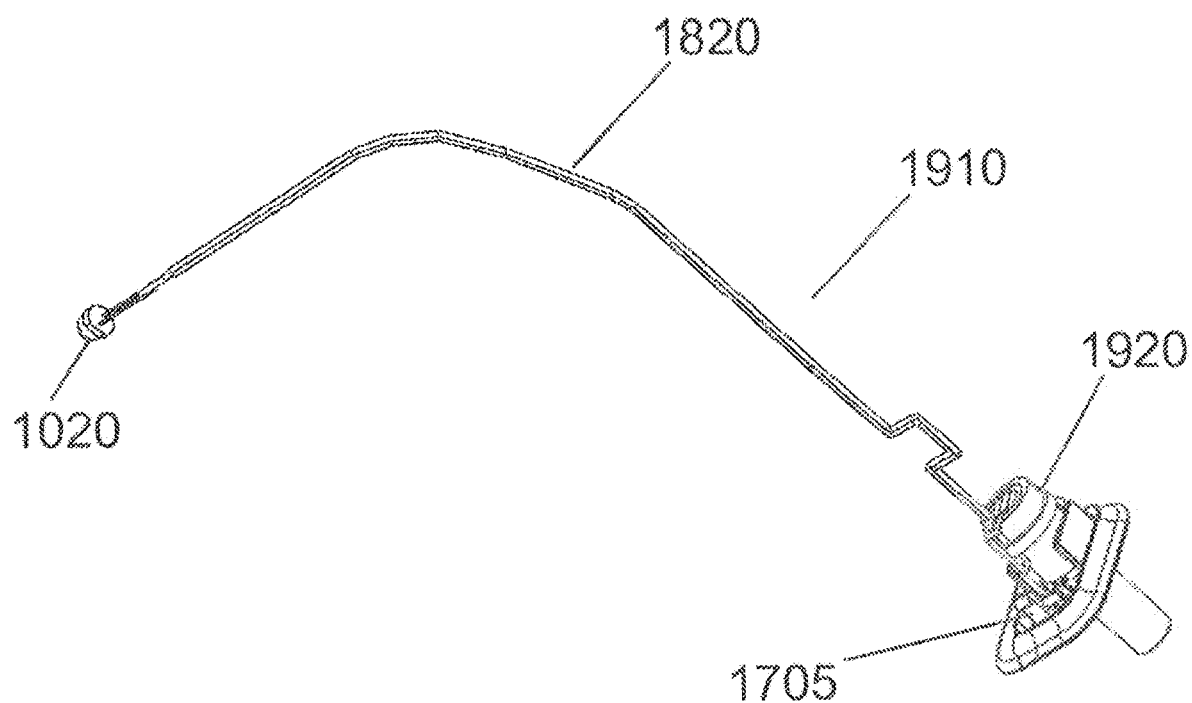
FIG. 19 is a side view of an exemplary embodiment.
Figure 20:
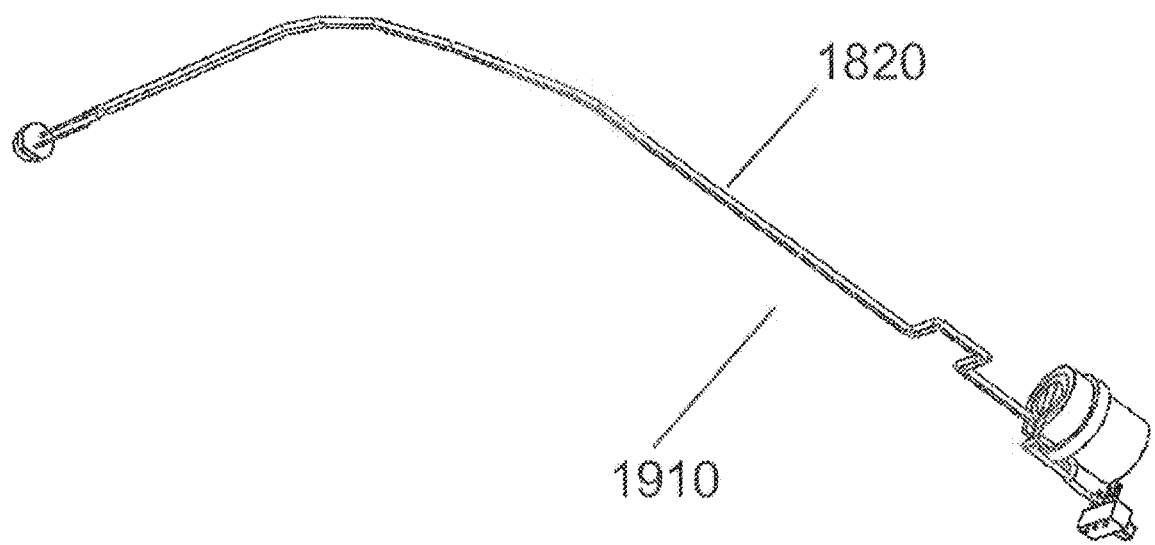
FIG. 20 is a side view of an exemplary embodiment.

FIGS. 18-20 illustrate the electrical connection to the light source 1020, which is normally held in place in channel 1105 by the smoke evacuation cover 1010. The wires 1820 lead from the light source 1020 into a power source in the handle 110. The power source is controlled by switch 1705. The power source may contain sufficient charge for only a single use.

As illustrated in FIG. 19, retractor 100 may include an assembly 1910. Assembly 1910 may be made or manufactured separate from the retractor body. Assembly 1910 may be include one or more of a power source 1920, wires 1820, switch 1705 and light source 1020.

In an exemplary method of manufacture, assembly 1910 may be inserted, as one pre-formed piece, into the base portion of handle 110. Assembly 1910 may be inserted into the cavity of handle 110 from the bottom, and fed up through handle 110, out the top portion of handle 110, adjacent to the saddle portion 210. The assembly 1910 may then be placed onto the barrel portion 215, within channel 1105, at which point the light source 1020 and wires 1820 of assembly 1910 are placed into receiving slots 1830. The cover 1010 is then placed over the channel 1105, including assembly 1910, and snapped into place.

A method of utilizing the smoke channel 1105 to remove the smoke from a physician's field of view may include the following. Generating smoke during a surgery or procedure by, for example, use of electro-cauterization tools. This smoke may interfere with the physician's vision, particularly with the field of view. The light source 1020 may be focused on the physician's field of view. During the course of the procedure, a vacuum source may be switched on, and smoke may be drawn into the retractor via the smoke evacuation channel. The smoke may traverse the smoke evacuation channel, into the handle, and out the bottom of the handle.

It should be noted that the entire retractor and associated components as disclosed herein, including the blade/handle, handle cover, and cover, are fully compatible with low-cost injection molding, and are able to be manufactured using low cost plastic. Further, the entire retractor assembly is optimal for use as a single-use and disposable product.

It should be understood that, among the advantages of the retractor, the need for a separate smoke evacuation tool is eliminated. Additionally, a bright light source is provided to illuminate the surgical cavity.

In an embodiment, the surgical retractor includes a handle portion joined to a blade portion. The blade portion may be perpendicularly joined to the handle portion, such as at a 90 degree angle or approximately 90 degree angle. In another embodiment, the blade portion may be joined to the handle portion at any suitable angle, such as, for example, a 30 degree angle, 45 degree angle, 110 degree angle or any other suitable angle.

In an embodiment, the blade portion includes a saddle portion, a curved barrel portion, an operative portion, and a channel cover. The saddle portion abuts the handle portion, forming a recessed cavity. The curved barrel portion is located distal to the saddle portion and defines a channel. Within the barrel portion, a light assembly is disposed. The operative portion is located distal to, and downwardly angled from, the barrel portion. The channel cover is disposed over the channel within the barrel portion, and is adapted to hold the light assembly in place.

In an embodiment, the operative portion of the retractor is substantially squared in shape, and includes a plurality of ridges distal to the barrel portion. The ridges may be of any suitable dimension. The ridges may be dimensioned to grip tissue and hold the tissue away from an operative area.

In an embodiment, the light assembly abuts the operative portion and includes a light source, a switch, a single-use power source, and a housing.

In an embodiment, the channel of the retractor is a smoke evacuation channel that extends from the barrel portion, through the saddle portion, and into a hollow space in the handle portion.

In an embodiment, the smoke evacuation channel extends through a length of the handle portion to a connector located at a bottom of the handle portion. A vacuum source may be coupled, via a connector, to the bottom of the handle portion. The coupling of the vacuum source provides a fluid connection between the smoke evacuation channel and the vacuum source, which provides suction for removing smoke.

In an embodiment, the surgical retractor includes a handle portion and a blade portion joined to the handle portion. The blade portion includes a saddle portion abutting the handle portion and forming a recessed cavity; a curved barrel portion located distal to the saddle portion and defining a channel, the barrel portion including a light assembly disposed within the barrel portion; an operative portion located distal to, and downwardly angled from, the barrel portion; a channel cover disposed over the channel, within the barrel portion, and adapted to hold the light assembly in place, the channel cover including a plurality of retaining tabs; and a plurality of retaining slots located on an underside of the blade portion, the retaining slots sized to minimize a size of the hole of the retaining slot and including a smoothed and raised geometry to facilitate tissue movement without catching. Each retaining tab is sized to fit into one of the plurality of retaining slots, and the retaining slots operable to hold the channel cover in place over the channel.

Therefore, provided is a self-lighted retractor with the ability to provide bright, shadow-less light to a surgical cavity. In accordance with the invention, also provided is a dual-purpose smoke evacuation channel and light source holder that couples the light source to the retractor. Further provided in accordance with the invention is a single-use battery and high volume moldable plastic components that allow for manufacture of a high-quality retractor that is affordable for single use, reducing infection risk. Yet further provided in accordance with the invention is an angled retractor blade that is squared, with integral ridges to hold tissue aside during use of the retractor.

In one or more embodiments, the blade, the handle and the curved section (referred to herein collectively as "the body") are integrally molded. In at least one exemplary embodiment, the material of which the body is formed is a strong, rigid, lightweight plastic (e.g., a polymer). One example of a suitable plastic is a glass-fiber reinforced polyarylamide compound that provides high strength and rigidity, surface gloss, and creep resistance. An exemplary embodiment uses a 50% glass-fiber reinforced polyarylamide compound, but those skilled in the art will understand that other percentages may be used without departing from the spirit and scope of the claimed invention.

Polyarylamides are thermoplastic crystalline polymers of aromatic diamines and aromatic dicarboxylic anhydrides having good heat, fire, and chemical resistance, property retention at high temperatures, dielectric and mechanical properties, and stiffness but low light resistance and processability. Those skilled in the art will understand that other plastics with suitable strength and rigidity also may be used.

In one or more embodiments, the body is made of a plastic (such as glass-fiber reinforced polyarylamide) having properties of at least one of radiolucence and nonconductivity. As used herein, "radiolucence" means high transparency to radiation, so that the device may be used when taking, for example, x-ray images. "Nonconductive," as used herein, means essentially dielectric.

Figure 23:
FIG. 23 is a fluoroscopy image illustrating the radiolucency of an embodiment.

An advantage of radiolucence is that the device may be used when taking X-ray images, without obscuring essential structures, as shown in FIG. 23. The "OBP" in FIG. 23 resulted from metal lettering placed below the blades of an embodiment to show the radiolucency. The much darker image on the left is of a stainless steel comparison blade, which shows up as black due to its opacity with respect to X-rays.

Embodiments described herein may provide light to the tip of the retractor and still remain highly (as much as 99%) radiolucent. Prior art devices have, for example, fiber optic cables that obstruct the view when X-ray images are taken, even when the devices are constructed of plastic. Metal devices are, of course, not radiolucent at all.

This radiolucent property means that retractors described herein may not need to be removed prior to the use of imaging techniques in surgical procedures. This can expedite the conduct of a procedure needing anatomic identification and/or device localization.

An advantage of nonconductivity is that it provides improved safety to patients—in contrast to metal retractors. Currents as low as 0.001 A may be felt by a patient, and larger currents may damage the patient. Embodiments described herein limit currents to less than $10^{-6}$ A, and thus greatly reduce electrical hazards.

For example, electro-cautery is used extensively in surgical tissue dissection. The use of metal retractors exposes the operating surgeon and the patient to the risk of retracted tissue damage due to destructive cautery current being conducted inadvertently. Retractors are often used to displace and retract delicate cautery sensitive tissues such small or large bowel (colon), lung, or major blood vessels. Cautery injury to these tissues can create major complications. In addition, retractors are often used to develop surgical tissue pockets in breast and pacemaker surgery. Use of a non-electrical conducting material, such as is described herein with respect to certain embodiments, prevents any stray electrical energy injury to the retracted tissues. Patient safety is thus enhanced.

As those skilled in the art will understand, strength is a function of both the material and the design. Designs using weaker material than is described herein need to be thicker and more rounded. Both of these traits will decrease the favorability of a retractor, which should not block visibility of the body cavity.

Flexural Strength represents the limit before a material will break under stress. Flexural modulus is the tendency of the material to bend under stress. Both of these parameters are critical to retractor design and resulting performance. First, a retractor blade must be thin enough to not interfere with the medical procedure for which it is used. Very thick blades will tend to fill the hole in the body that the physician needs to work in. An optimal design will have a blade thin enough to allow space for the physician to work. Typically metal blades are used because of their high Flexural modulus. They have unlimited flexural strength, because they bend rather than break. Metal blades as thin as 0.5-2 mm are readily available and this thickness is small enough to not interfere with the physician's work space in a wound or operating cavity. Stainless steel metal can have a flexural modulus of 180 Gpa which will inhibit blade deformation of more than 10 mm under 15 lbs of tip pressure for most retractor designs.

Plastic injection molded blades require a thicker blade because they have a lower Flexural Modulus. Blade strength will increase as the cube of the blade thickness, but blade thicknesses larger than 2 mm are not desirable in most physician applications. Typical plastic materials, such as those shown in Table 1 below, have a Flexural Modulus of just a few Gpa and a Flexural Strength of less than 200 Mpa. These lower value parameters result in retractor blades that deform more than 10 mm under use, and are likely to break with less than 30 lbs of force placed on the tip of an average length retractor blade (50-150 mm long).

Retractor blades that deform significantly during use increase the physician's difficulty in retracting the tissue during a medical procedure. Retractor blades that break with less than 30 lbs of force can create a hazard to the patient since a broken blade, or pieces of a broken blade, may fall into the patient and create damage. Retractor blades made from the plastics listed in the following table will typically bend more than 20 mm under 10 lbs of tip force, and will break at 15 lbs (or even less) of tip force.

TABLE 1

TYPICAL FLEXURAL STRENGTH AND FLEXURAL MODULUS OF POLYMERS

| POLYMER TYPE | FLEXURAL STRENGTH (MPa) | FLEXURAL STRENGTH (MPa) |
|---|---|---|
| Polyamide-lmide | 175 | 5 |
| Polycarbonate | 90 | 2.3 |
| Polyethylene, MDPE | 40 | 0.7 |
| Polyethylene Terephthalate (PET) | 80 | 1 |

Figure 24:
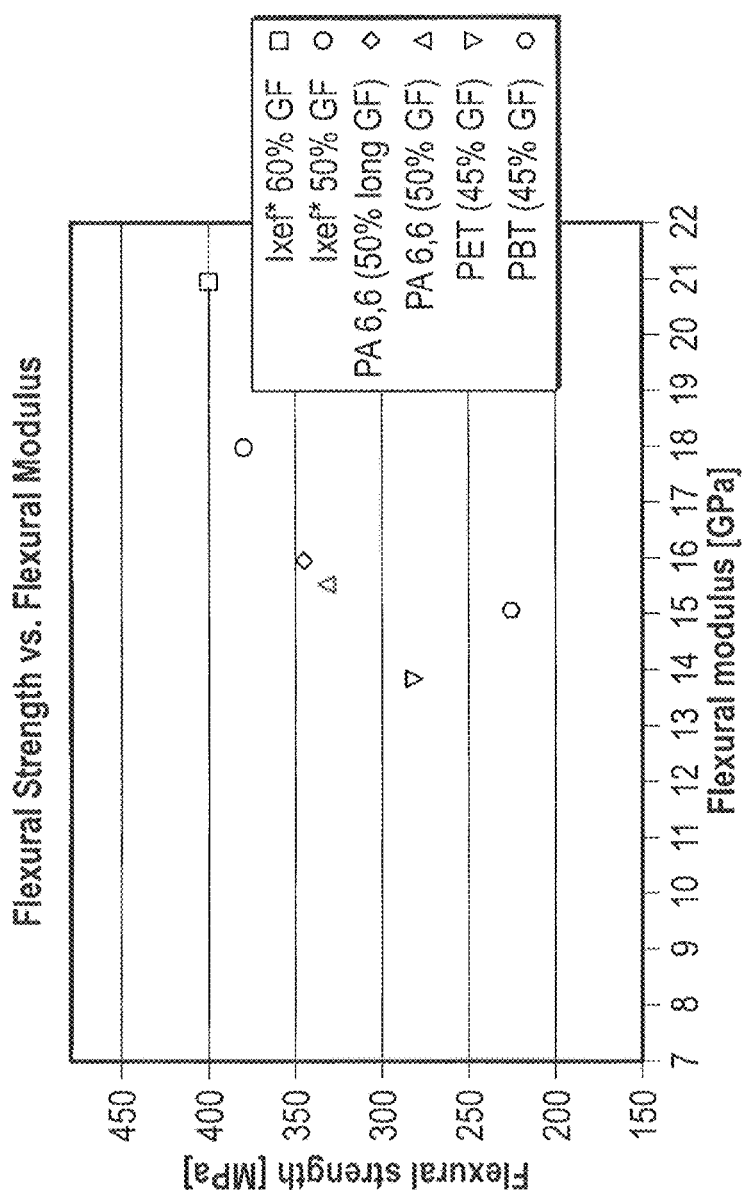
FIG. 24 illustrates flexural strength and flexural modulus for a variety of plastics.

To increase the flexural modulus and flexural strength of plastic, in an embodiment, glass fiber is added to the plastic material. FIG. 24 shows a variety of plastics with various percentages of glass fiber added.

It can be seen from the above that the addition of glass fiber can increase the Flexural Strength of certain plastics to 300 Mpa or above, and increase the Flexural Modulus to 16 Gpa or above. In an exemplary embodiment, a certain type of plastic, polyacrylamide, is infused with glass fiber to create a flexural strength of over 375 Gpa and a Flexural modulus of over 17 Gpa.

Plastics with these properties have the ability to create retractor blades of approximately 2 mm thickness that withstand over 30 lbs of tip force without breaking and deform less than 10 mm under 15 lbs of force. Additionally, the glass fiber in this material will "glassify" at the surface leaving a very smooth "metal like" finish which is highly desirable in retractor applications.

The glass fiber in the material also will decrease the likelihood of sharp shards of material being created during an overstress and breakage event. This tendency to create dull edges upon breakage decreases the likelihood that a patient will experience damage if the retractor is overstressed and ultimately broken.

Additionally, the way in which a material breaks can be important in medical applications. The breakage characteristics of a material are often measured by Impact Strength. Materials with low impact strength (10-20 J/M) can break under stress into large numbers of sharp shards which can pose a hazard to a patient if material failure occurs during a medical procedure. Sharp shards can cut patient tissue and large numbers of these shards can make it difficult or impossible to remove the broken material from the patient.

Materials (such as glass fiber reinforced polyarylamide) used in certain embodiments described herein have a high impact strength (>100 J/M) and will fail with very few fractured component edges (and the resulting edges will be blunt). This breakage characteristic minimizes potential hazard to a patient during product overstress that results in material breakage.

FIGS. 25-33 provide views of other exemplary embodiments.

Figure 25:
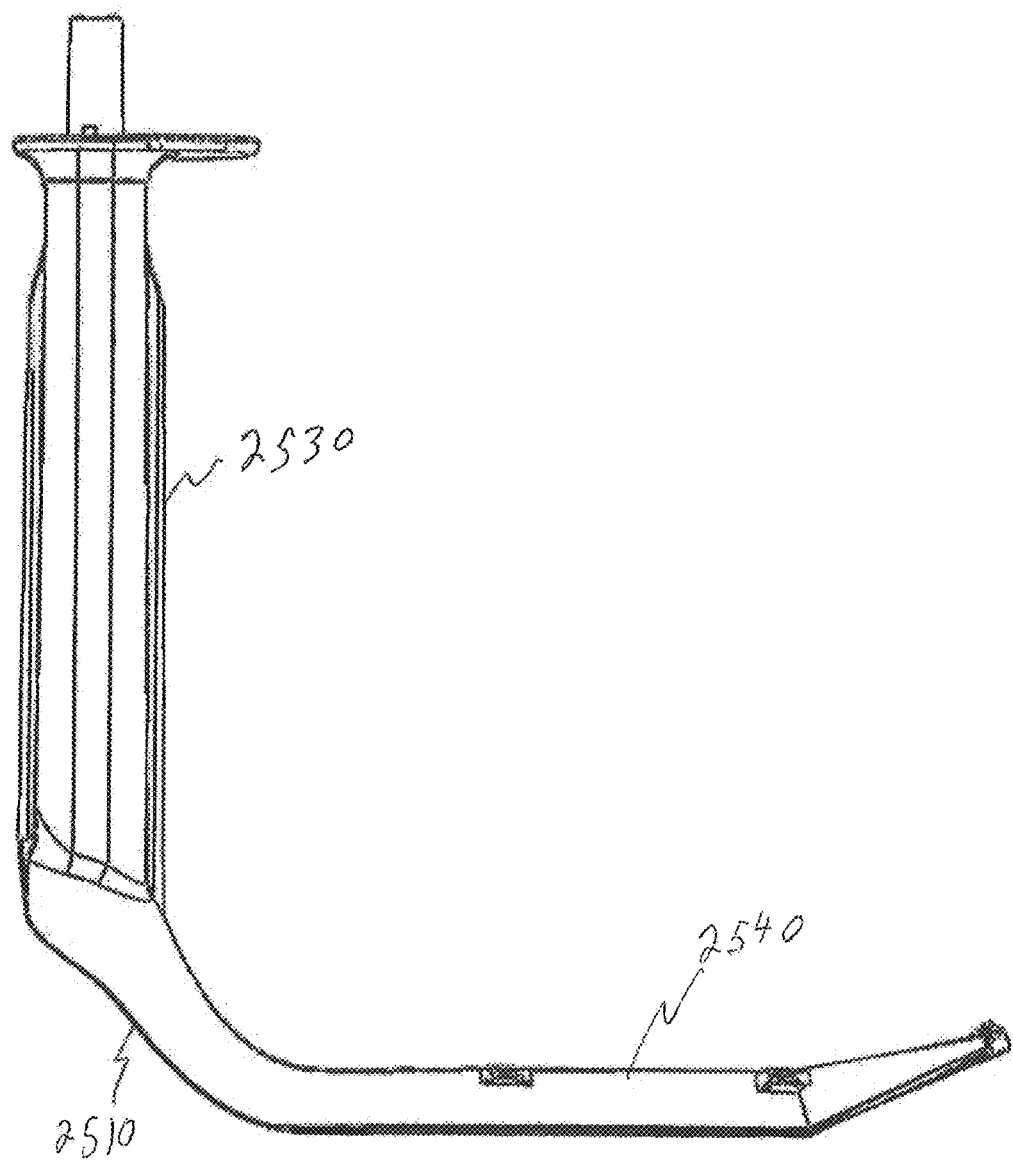
FIG. 25 is another view of an exemplary embodiment.
Figure 26:
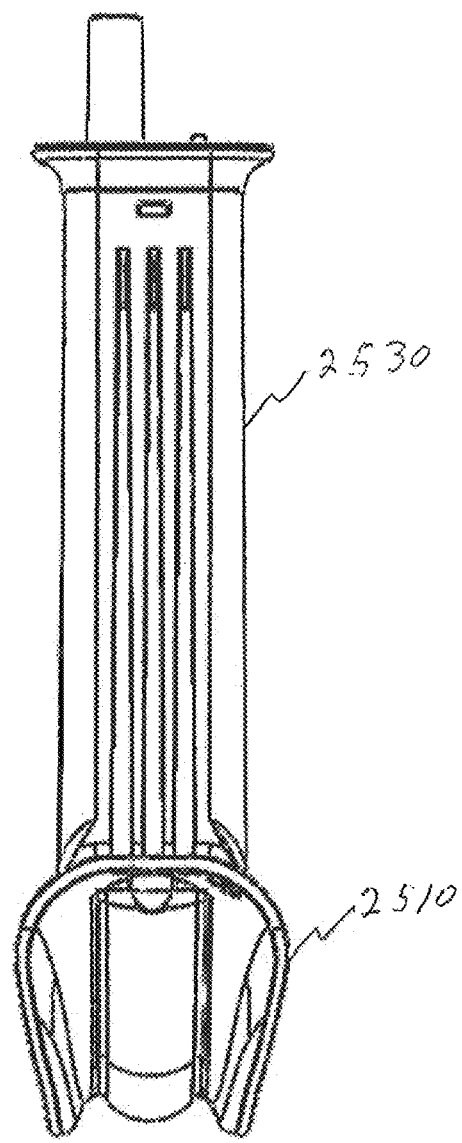
FIG. 26 is another view of an exemplary embodiment.
Figure 27:
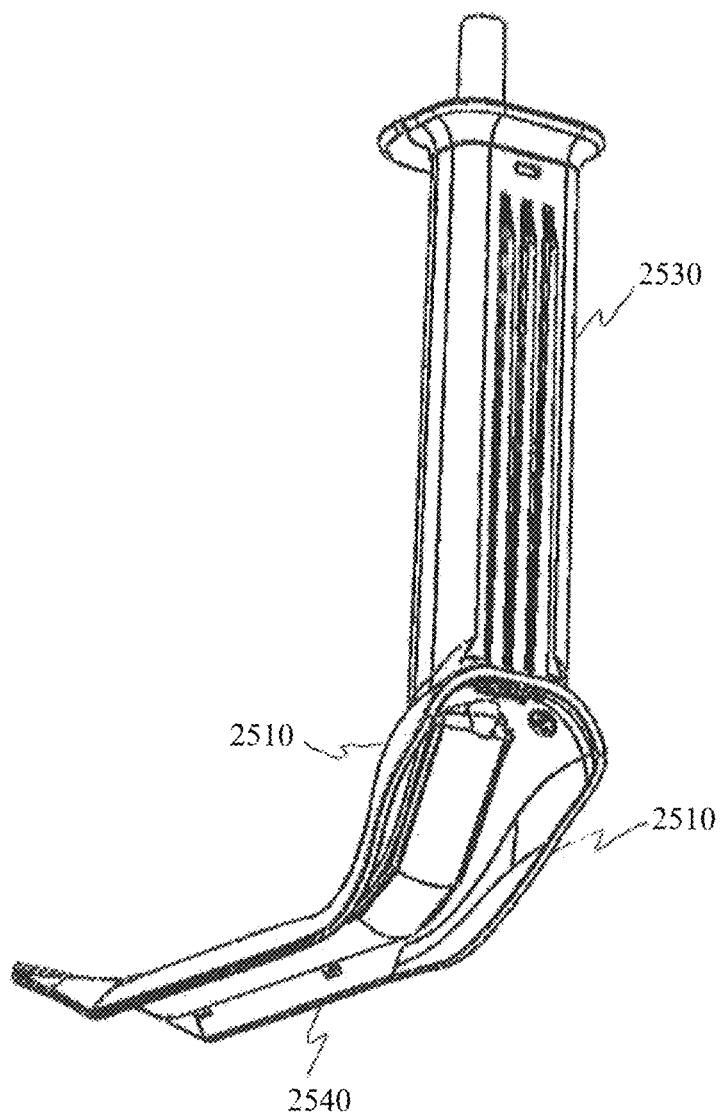
FIG. 27 is another view of an exemplary embodiment.

FIGS. 25-27 depict a breast retractor with flanges 2510 at the joint (saddle) between the handle 2530 and blade 2540. The flange sizes are greatly reduced in comparison to those for the embodiment depicted in FIG. 2, for example, yet the strength of the retractor has been maintained.

Figure 28:
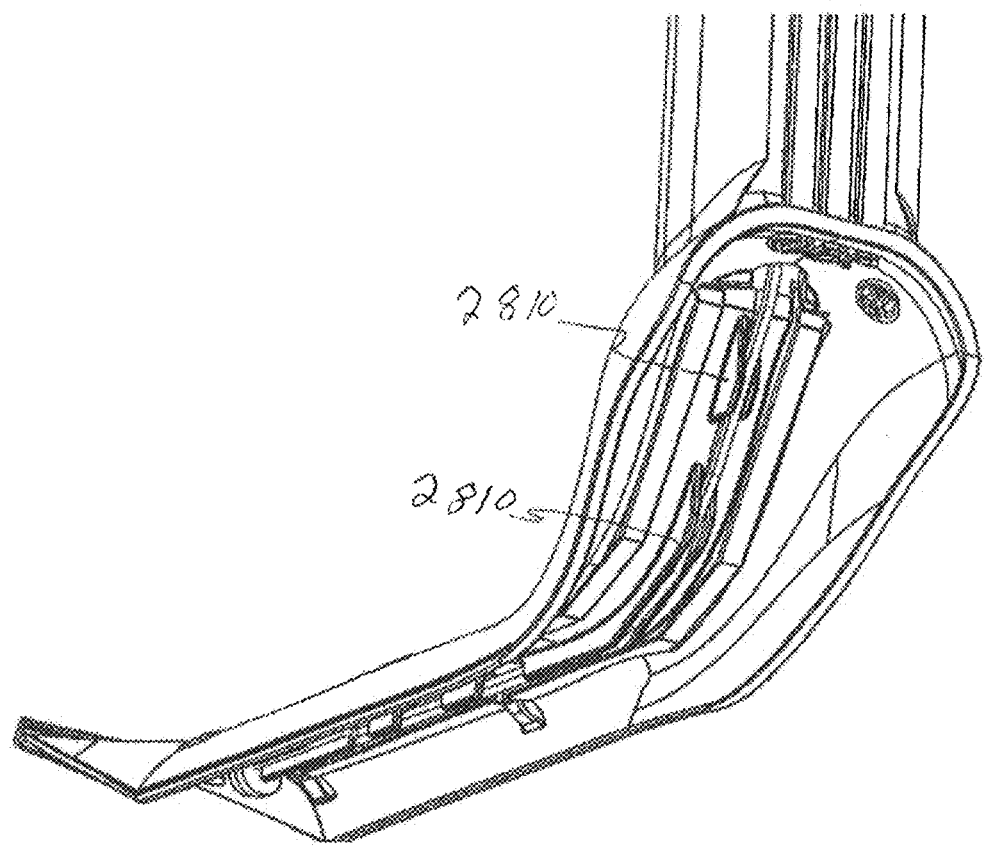
FIG. 28 is another view of an exemplary embodiment, with a light/smoke evacuation cover removed.

FIG. 28 is another view of an exemplary embodiment, with a light/smoke evacuation cover removed. Parallel guides 2810 down the center of the blade and into the saddle hold the LED wires in place. These guides also strengthen the joint between the blade and handle so that the retractor remains strong even when the side flanges are dramatically reduced in size to improve physician visibility with angled views.

These wire guide walls are made thicker and higher to add strength to the curved section that was removed by the reduction of the flanges. The first design (see FIG. 32) can withstand over 40 lbs of pressure on the distal end of the blade. The new reduced flange design (see FIG. 33) can likewise withstand over 40 lbs of pressure, due to the increased structure in the wire guides. The wire guides thus serve two functions: (a) to guide the LED wires, and (b) to add strength to the curved portion between the handle and blade.

Figure 32:
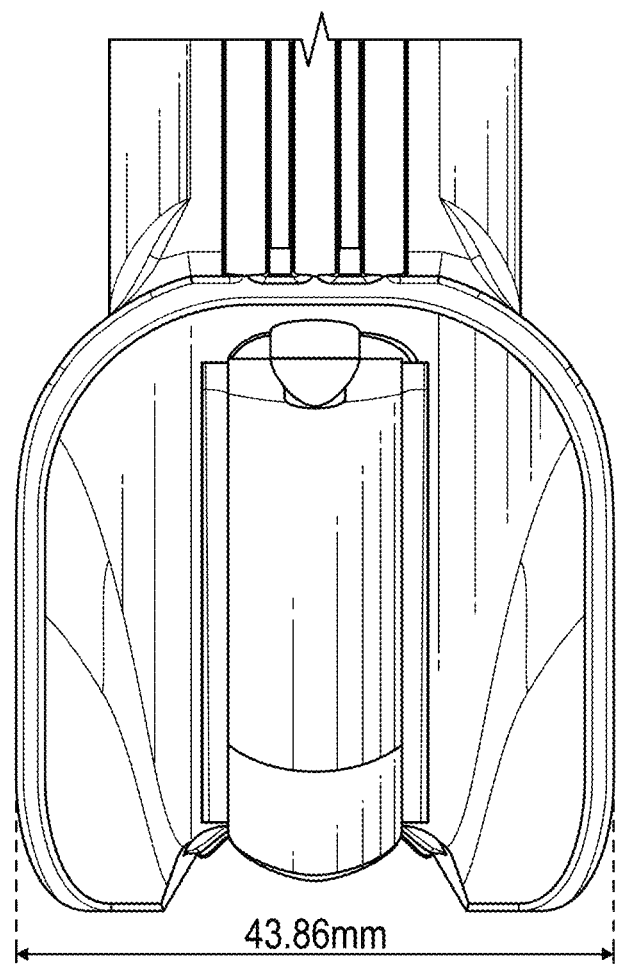
FIG. 32 is a perspective view of a first exemplary embodiment.
Figure 33:
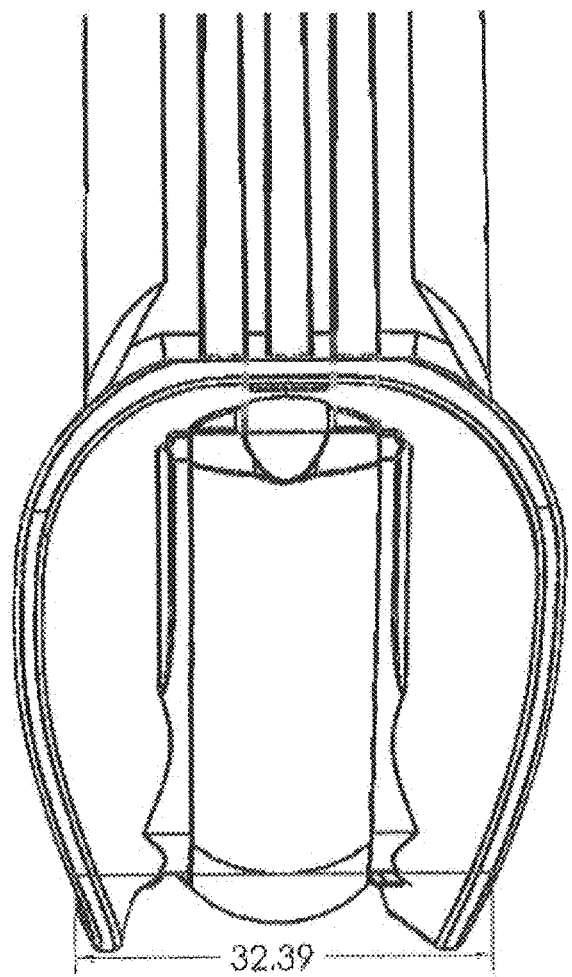
FIG. 33 is a perspective view of a second exemplary embodiment.

The increased visibility can be seen via comparison of FIGS. 32 and 33. In the design depicted in FIG. 32, the effective blocked view is 43.86 mm. In the design depicted in FIG. 33, the effective blocked view is 32.39 mm—resulting in a greater than 25% decrease in visual obstruction. The lower part of the saddle portion in each of FIGS. 32-33 is the barrel end, and the upper part of the saddle portion is the handle end (the topmost portion of each figure depicting a portion of the handle).

When looking at the side of the retractor in FIG. 33, the effective height of the blade is the distance between the bottom of the blade to the top of the barrel wall. In general a larger distance will produce a stronger blade—i.e., the strength is related to the effective "thickness" of the structure. Because of the leverage created by the blade, any force placed on the distal tip of the blade will create an increasing stress moving from the distal end to the proximal end. That is why the proximal end must have a larger effective structural thickness than the distal end. The flanges provide this larger effective thickness.

Figure 29:
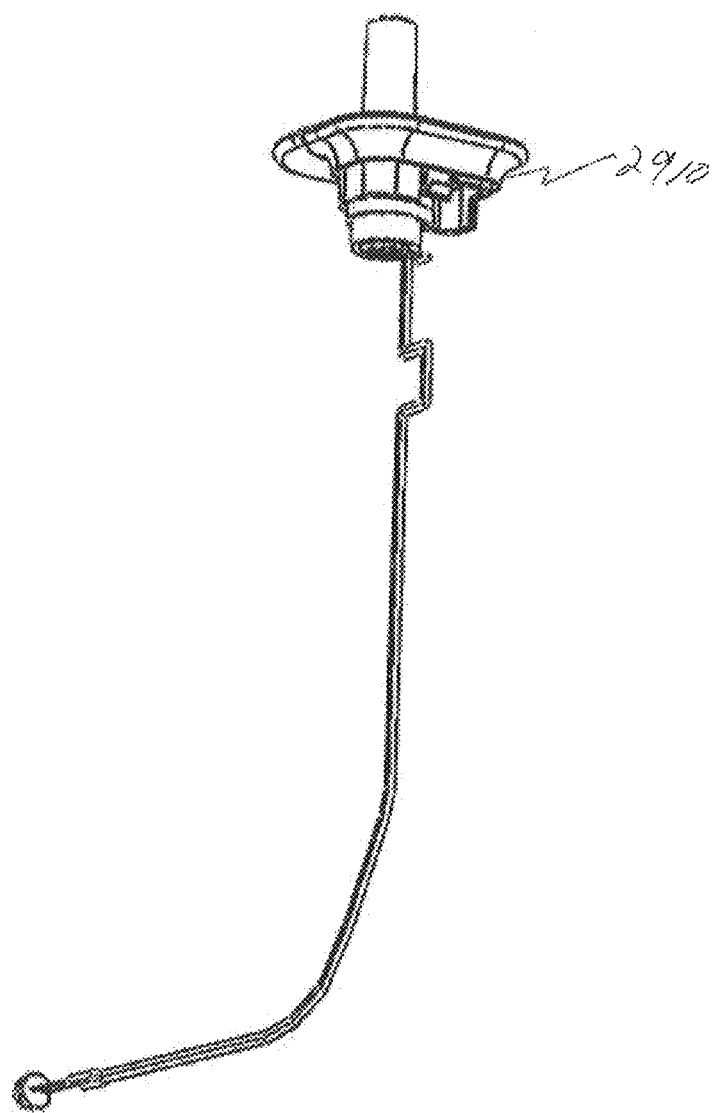
FIG. 29 depicts an end cap assembly of an exemplary embodiment.

FIG. 29 depicts an end cap assembly 2910 of an exemplary embodiment. The end cap may perform LED switching, smoke evacuation, and/or electrical component holding functions. In the depicted embodiment, all three functions are performed.

Figure 30:
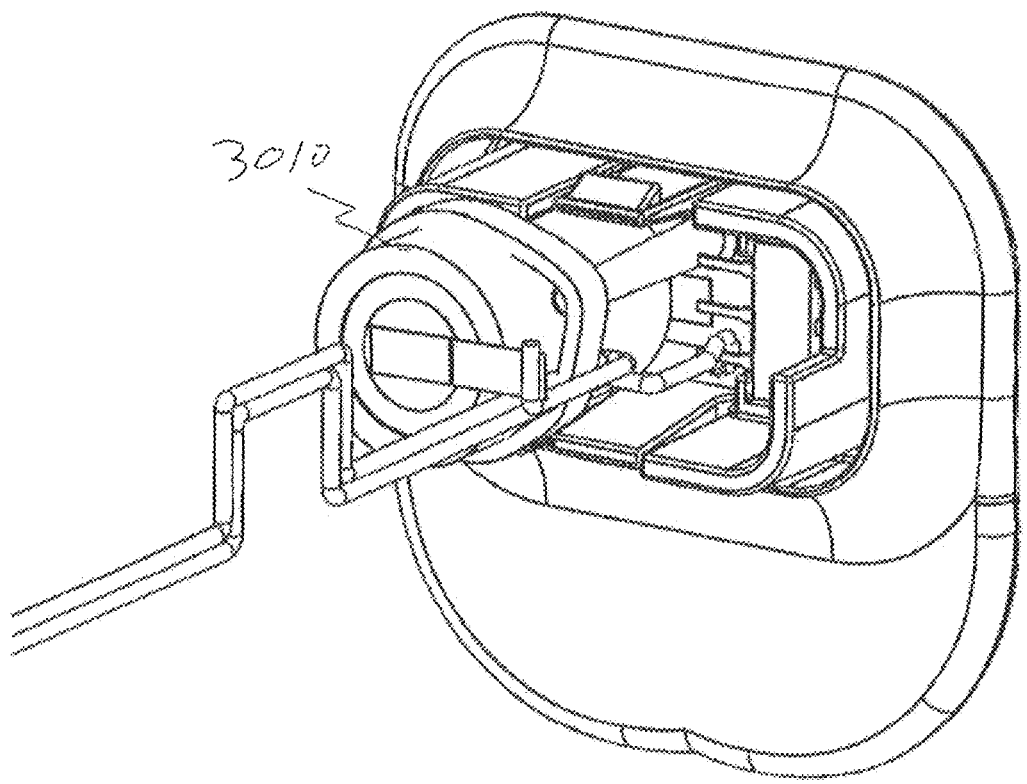
FIG. 30 is another view of an end cap assembly of an exemplary embodiment.

FIG. 30 is a close-up view of an end cap assembly of an exemplary embodiment. Item 3110 with the tab on the top and bottom is a battery assembly. The tabs may be made of metal and soldered to the wires as shown (one of the metal tabs soldered to the center leg of the switch). There may be an elastic around the battery assembly that holds it to a molded post during assembly so that the battery assembly does not move. Wires are shown soldered to the metal tab of the battery assembly and to one of the leads of the switch.

Figure 31:
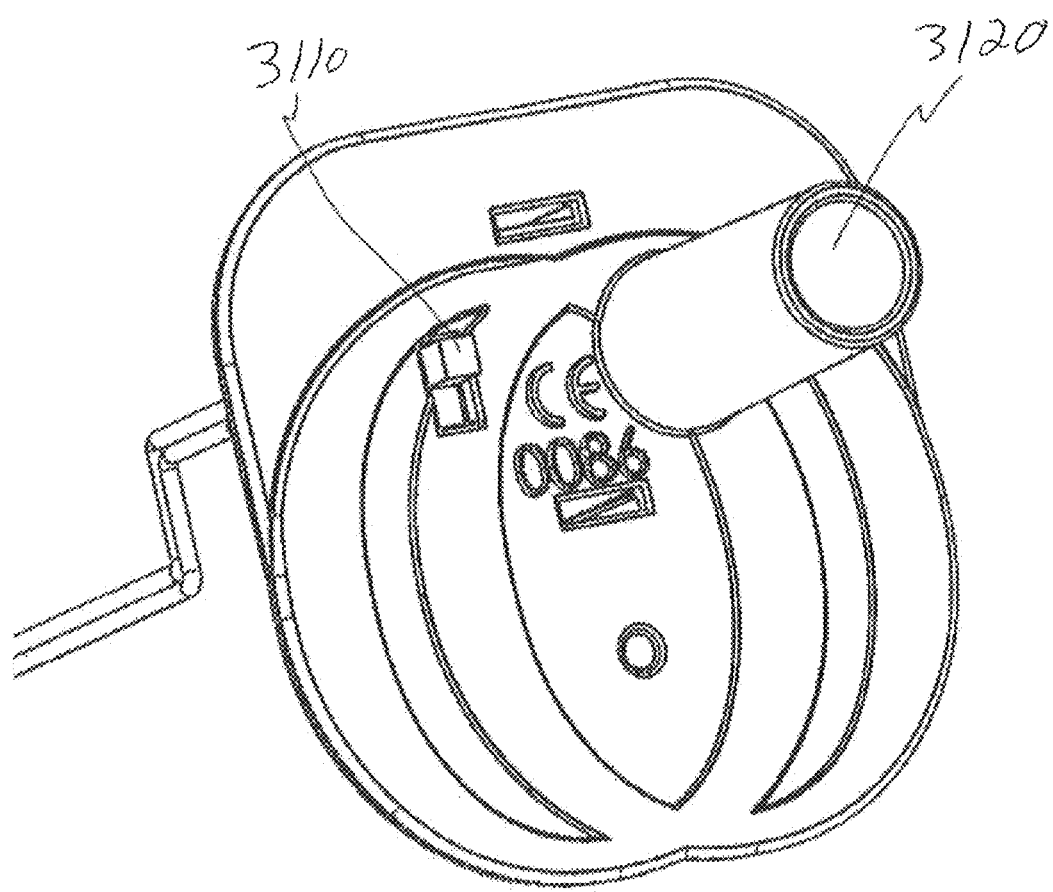
FIG. 31 is another view of an end cap assembly of an exemplary embodiment.

FIG. 31 is a view of an exemplary end cap assembly from the other side, showing a switch tab 3110 and smoke evacuation fitting 3120.

Figure 34:
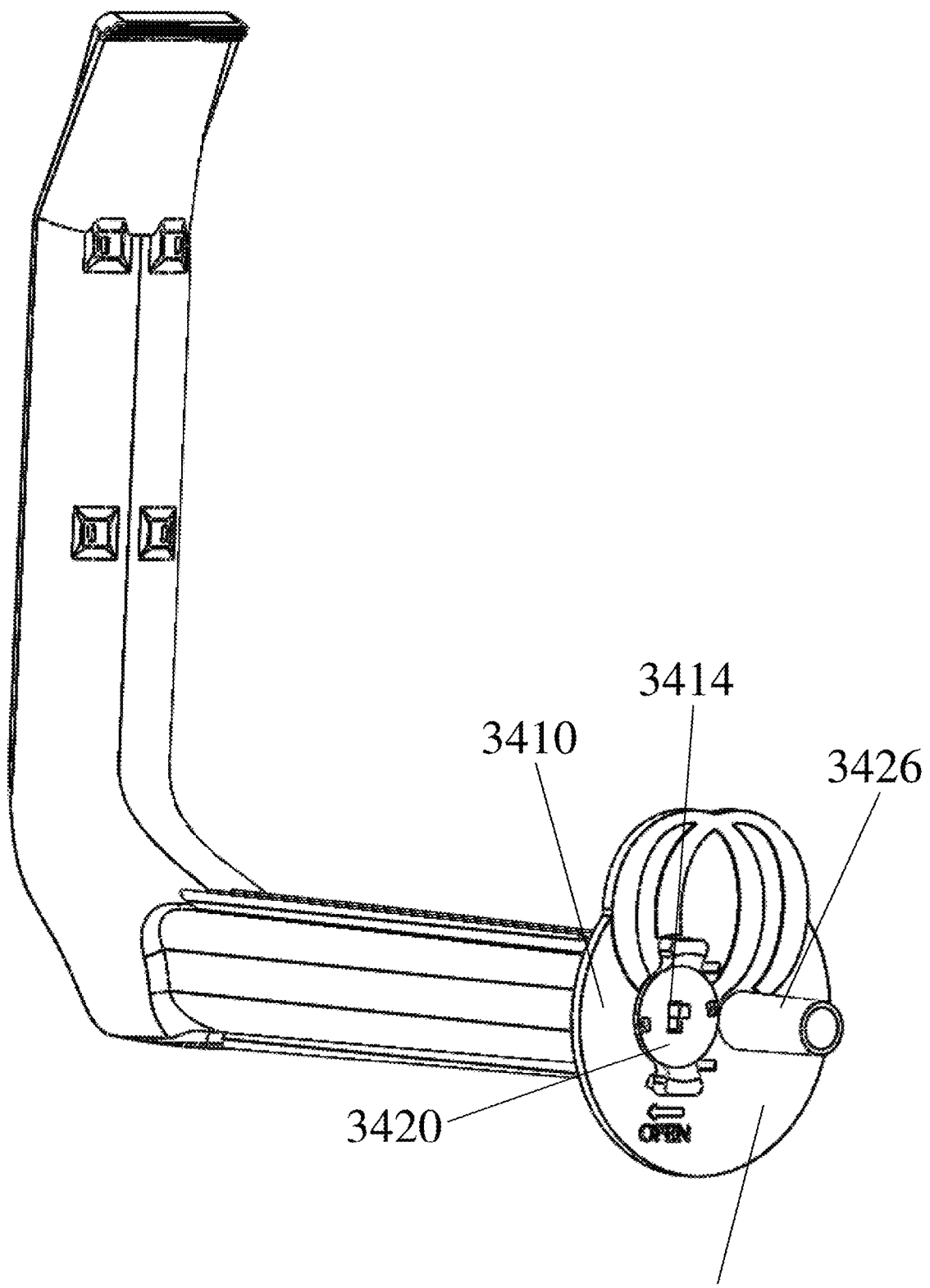
FIG. 34 is a perspective view of an end cap assembly in accordance with a further embodiment including a releasable battery door.

FIGS. 34-38 depict a further embodiment of an end cap assembly coupled to a retractor handle or to any other medical device with a hollow handle. As shown in FIG. 34, an end cap assembly 3410 incorporates some of the features of the previously-described design, with added features of airtight construction, airtight coupling with a retractor handle and use of a releasable battery door 3420. The releasable battery door 3420 is operated to allow one or more batteries held by the end cap assembly 3410 to be removed and disposed without the remaining portions of the end cap assembly 3410 being separated from the retractor. In this and other embodiments of the end cap assembly described herein, in order to withstand significant force during use of the retractor, the end cap assembly is coupled to the retractor so that the end cap assembly is very difficult, if not impossible, to remove. Hence, without a releasable battery door, the retractor is disposed, after it is used, together with the end cap assembly still intact and also with the batteries. However, there is an environmental need for disposing of batteries separately from the retractor after use in order to recycle them, and the embodiment shown in FIGS. 34-38 provides an exemplary solution by using a releasable battery door, which creates an opening in the end cap assembly through which the batteries can be dropped and disposed separately. In this embodiment, the releasable battery door can be opened easily by a user wearing gloves and the batteries can be removed from the retractor without the user coming into contact with the batteries, thus avoiding contamination of the batteries with medical waste. In addition, the end cap assembly 3410 includes a suction port 3426 which can be connected to a suction or vacuum source to allow for removal of debris and smoke as described above. The airtight construction of the end cap assembly 3410 improves the suction operation and removal of debris and smoke by eliminating air gaps that would otherwise cause a reduction in the suction strength.

FIGS. 35A-35B show an internal configuration of the end cap assembly shown in FIG. 34. As illustrated in FIG. 34 and FIGS. 35A-35B, the end cap assembly includes an outer cover 3412 having a first, outer-facing, surface 3412a and a second surface 3412b opposing the first surface and facing the handle of the retractor. As shown in the cross-sectional view of FIG. 35B and in FIG. 34, the releasable battery door 3420 is inserted into an opening in the outer cover 3412 and engages with the outer cover 3412. The end cap assembly 3410 also includes an activation device, such as an activation switch 3414, and associated circuitry and wiring, with a portion of the activation switch protruding through an opening formed in the releasable battery door 3420. In this illustrative embodiment, the activation switch 3414 can be moved between an ON position and an OFF position to turn on and turn off a light source of the retractor. In other embodiments, the activation switch 3414 can be in any other suitable form, including, but not limited to a removable tab or a push button.

As further shown in FIGS. 35A-35B, the end cap assembly includes an outer wall structure 3416 and an inner wall structure 3418 extending outwardly from the second surface 3412b of the outer cover 3412. The outer wall structure 3416 and the inner wall structure 3418 form a channel therebetween which is adapted to receive an end portion of the retractor handle. In this way, when the end cap assembly 3410 is coupled with the retractor handle, the inner wall structure 3418 and any components held therein are disposed within the retractor handle, while the outer wall structure 3416 is disposed outside of the retractor handle. Secure coupling between the end cap assembly 3410 and the retractor handle is achieved by using one or more latches 3422 provided in the end cap assembly 3410 which are adapted to engage with corresponding openings formed in the retractor handle. As shown in FIG. 35A, the latches 3422 may be disposed in spaces formed between portions of the inner wall structure 3418. Alternatively, latches 3422 may be incorporated into the inner wall structure 3418, provided they have sufficient flexibility to deform for engagement with the corresponding openings. For example, the latches 3422 may be formed within the inner wall structure, wherein the inner wall structure has a cutout partially around each latch to provide flexibility. Configuration of the latches 3422 and their airtight properties are described herein below with respect to the embodiment shown in FIGS. 39-43.

As further shown in FIGS. 35A-35B, the end cap assembly 3410 of this embodiment includes a battery assembly 3510 held and partially enclosed by the inner wall structure 3418. The battery assembly 3510 includes one or more batteries for powering a light source of the retractor's illumination assembly. The batteries that may be used to power the light source have been described in reference to previous embodiments and further descriptions thereof will be omitted. The battery assembly 3510 may also include wiring and circuitry, if necessary for electrically coupling the batteries to electrically couple with other components of the retractor, such as the wires, the activation switch, etc. as shown and described in reference to previous embodiments. In one illustrative embodiment, the battery assembly 3510 further includes a biasing member, such as a spring 3530, that presses the batteries against the releasable battery door 3420 to force an electrical connection with an activation switch 3414 positioned at the other end of the battery assembly 3510 and/or to assist in removal of the batteries after the releasable battery door 3420 is opened or removed from the end cap assembly 3410.

As shown in FIGS. 35A-B, the battery assembly 3510, including the batteries and the spring 3530, is enclosed or partially enclosed by the inner wall structure 3418 of the end cap assembly 3410. In this way, the batteries and the spring are held in place by the inner wall structure 3418 and are prevented from shifting during use of the retractor. In this illustrative embodiment, an electrical connector 3424 is provided in the inner wall structure for electrically connecting the batteries via the spring 3510 with one of the wires leading to the light source. In other embodiments, the spring 3510 may be directly coupled with the wire leading to the light source, without the use of a separate electrical connector.

As can be seen in FIG. 35A, the inner wall structure 3418 also encloses or partially encloses a region in direction communication with the suction port 3426. In this embodiment of the end cap assembly, the battery assembly and the activation switch are disposed to the side of this region and do not overlap with the suction port 3426. This configuration allows for stronger suction without interference from other components of the end cap assembly. In addition, by placing the one or more batteries in an overlapping relationship to the activation switch, as described herein below, the end cap assembly is airtight and prevents or reduces air leaks through the opening for the switch. This also improves the suction and removal of debris and smoke during use of the retractor. In some embodiments, the battery assembly may be placed so as to partially overlap with the suction port 3426, if needed to comply with size limitations of the end cap assembly.

FIGS. 36A-36B further illustrate a portion of the end cap assembly 3410 that includes the battery assembly 3510, the activation switch 3414 and the releasable battery door 3420. Specifically, FIGS. 36A-36B show the positional relationship among the batteries in the battery assembly 3510, the activation switch 3414 and the releasable battery door 3420. In the exemplary embodiment shown in FIGS. 36A-36B, the activation switch 3414 is arranged in the releasable battery door 3420, so that an opening is provided in the releasable battery door 3420 for a switch operating member 3414a of the activation switch 3414. In this illustrative embodiment, the switch operating member 3414a extends through the opening in the releasable battery door 3420 and can be moved between the ON and OFF positions within the opening. As also shown in FIGS. 36A-36B, wiring 3414b, including wire loops, for the activation switch 3414 is provided on the internal side of the releasable battery door 3420 and is attached to the releasable battery door 3420 by an electrical connection plate 3424. The wiring 3414b is electrically coupled with one of the wires connected to and leading to the light source.

The battery assembly 3510 is positioned so that the one or more batteries abut the electrical connection plate 3424 and/or wiring 3414b when the releasable battery door 3420 is closed. As can be seen in FIGS. 36A-36B, the spring 3530 biases the one or more batteries at the other end in a direction toward the releasable battery door 3420. In this way, an electrical connection is made between the activation switch 3414 and the one or more batteries via the electrical connection plate 3424 and/or the wiring 3414b and when the releasable battery door 3420 is opened, the batteries are forced out by the biasing force of the spring. Accordingly, without the releasable battery door surface to which the batteries are pressed against, the batteries will drop loose without any additional effort. By placing the batteries over the activation switch 3414 provided in the releasable battery door 3420, an airtight construction is achieved so that suction through the suction port 3426 is not reduced by air leaks through the opening in the releasable battery door. In addition, such configuration greatly reduces the number of necessary components to allow for battery disposal via the releasable battery door.

As shown in FIGS. 36A-36B, the releasable battery door 3420 includes a pair of side tabs 3421, each of which extends from a side of the releasable battery door 3420. Each of the side tabs 3421 includes a latch protrusion 3421a which is adapted to engage with a corresponding opening 3412c in the outer cover 3412, which are shown in FIG. 37.

Figure 37:
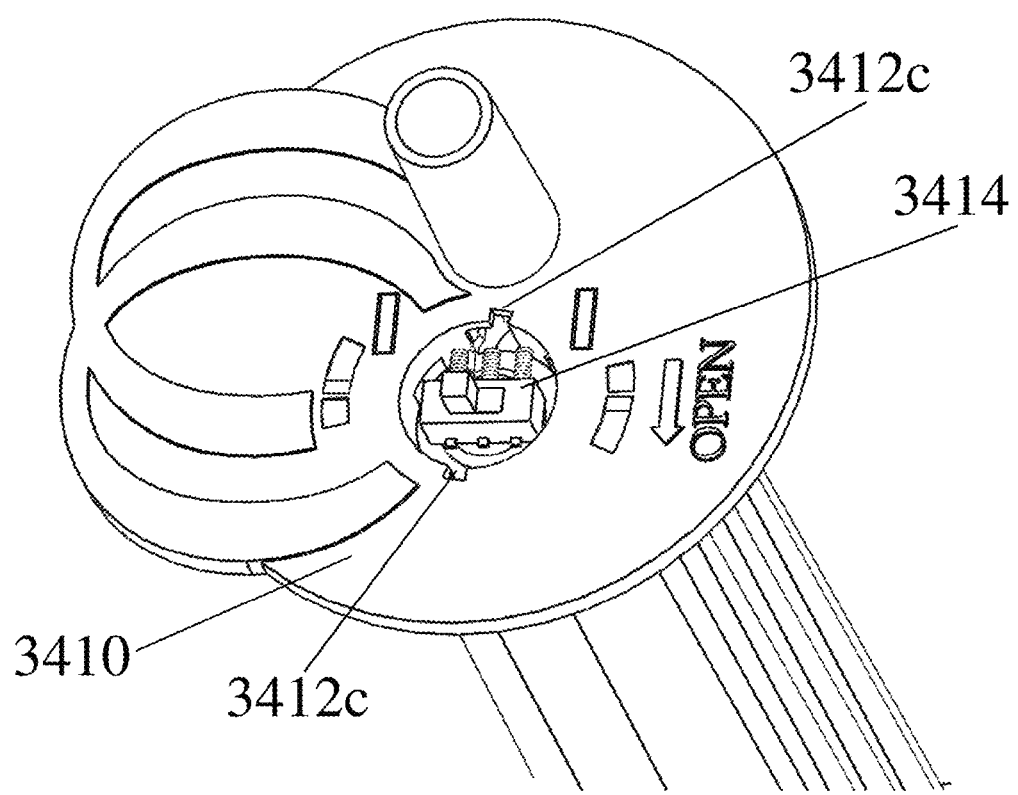
FIG. 37 is another perspective view of the end cap assembly of FIG. 34 with the releasable battery door removed to expose the activation switch.

FIG. 37 shows the end cap assembly 3410 with the releasable battery door 3420 removed so as to expose the activation switch 3414. The releasable battery door 3420 is attached or closed by rotating it relative to the outer cover 3412 which causes the latch protrusions 3412 inserted into the corresponding openings 3412c to engage with the outer cover 3412. The outer cover may include corresponding recesses adjacent to the openings 3412c to facilitate engagement with the latch protrusions. The side tabs 3412 of the releasable battery door 3420 make it easy for the user to rotate the releasable battery door 3420 between the closed position and the open position. In the illustrative embodiment shown, the releasable battery door 3420 can be removed from the end cap assembly 3410 by rotating it about 15 degrees from its original (closed) position. In some other versions, the releasable battery door may be operated by pressing, pulling, peeling, or breaking, etc. the releasable battery door. As discussed above, upon removal of the releasable battery door, the spring pushes out the batteries contained in the battery assembly of the end cap assembly, and the batteries are disposed. In versions where a spring is not used, a user may need to shake or apply a small force to the retractor to trigger the batteries to drop from the battery assembly.

Figure 38:
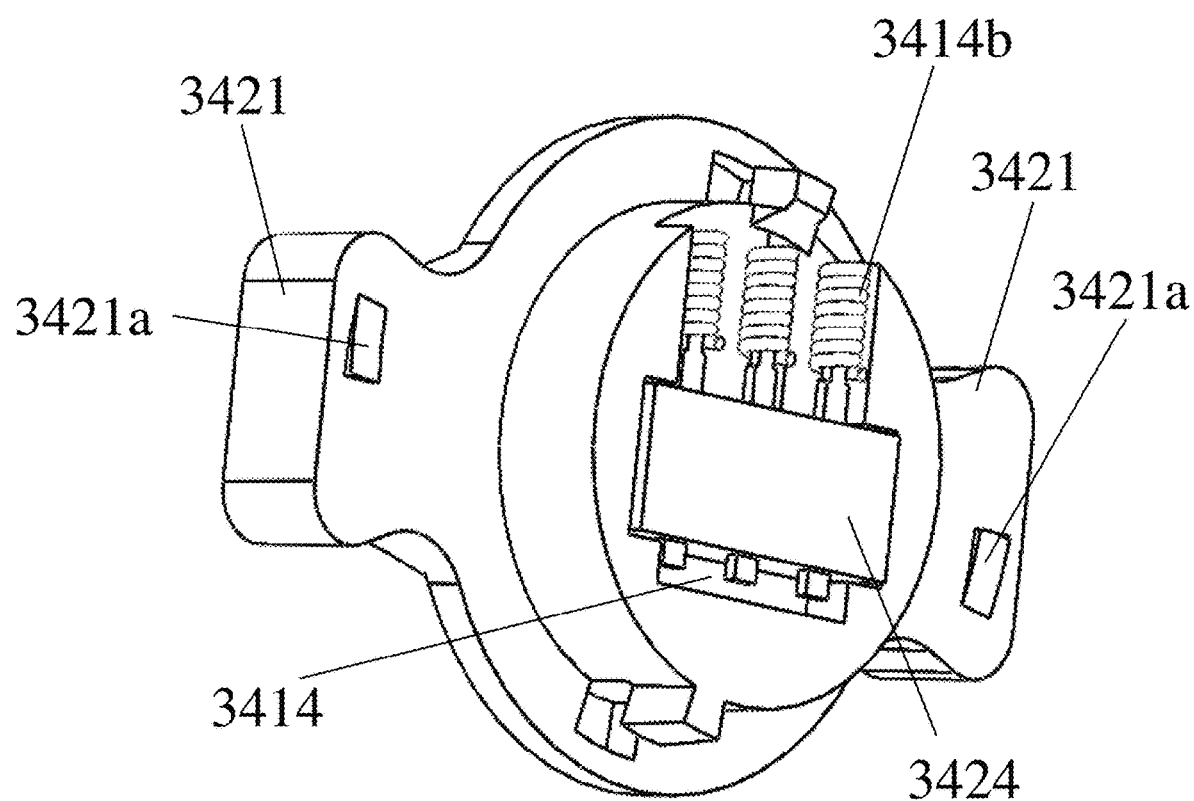
FIG. 38 is an internal view of the releasable battery door of the end cap assembly of FIG. 34 with the activation switch.
Figure 39:
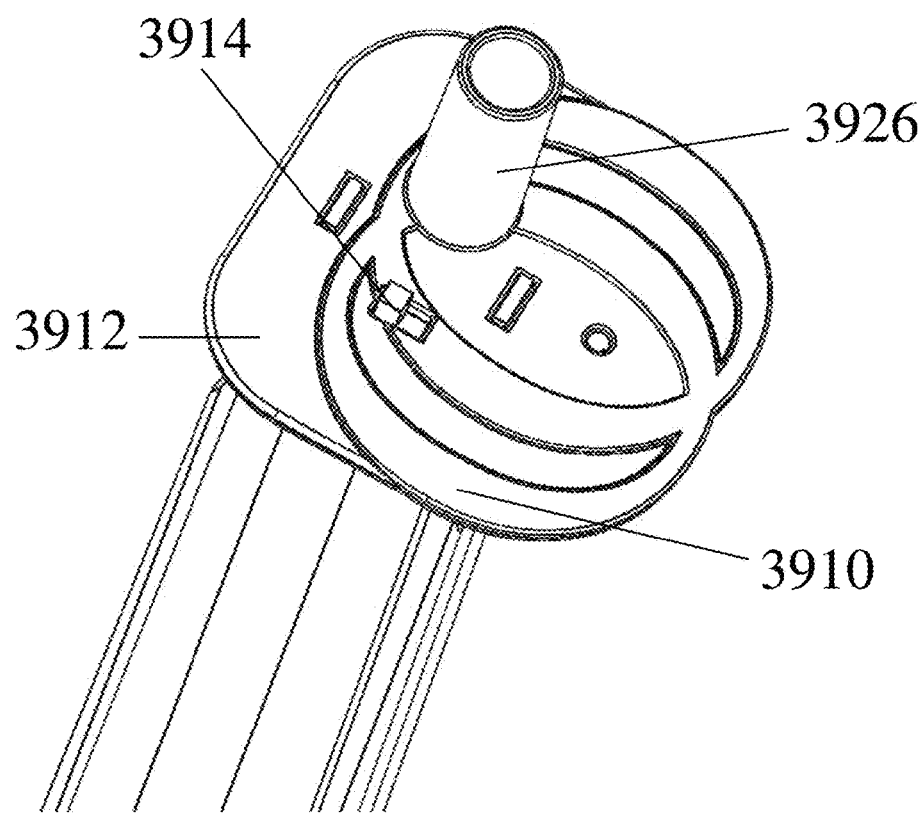
FIG. 39 is a perspective view of an end cap assembly in accordance with a further embodiment including an end cap port.

FIG. 38 shows an internal view of the releasable battery door 3420 that has been removed. As described above, the activation switch 3414 is provided in the releasable battery door 3420, and as shown, the wiring for the activation switch 3414b is held by the electrical connection plate 3424 and attached to the releasable battery door 3420. When the releasable battery door 3420 is attached to the end cap assembly, the wiring 3414b for the activation switch is electrically coupled to the wiring leading to the light source of the retractor and is electrically coupled to the one or more batteries of the battery assembly.

In one version, the releasable battery door 3420 completely detaches from the end cap assembly 3410 and is disposed separately. In this illustrative embodiment, the activation switch and/or the wires used in conjunction with activation switch and the batteries to power the light source remain connected to the releasable battery door 3420 and are removed from the end cap assembly 3410, and the batteries can be disposed and recycled. In another embodiment, the releasable battery door 3420 remains attached to (or remains hanging from) the end cap assembly 3410 via a wire, string, a hinge or other suitable technique to allow only the batteries to be disposed separately. In such embodiment, the batteries are disposed without requiring the user to ensure that the releasable battery door 3420 is not disposed together with the batteries.

FIGS. 39-43 depict another embodiment of an end cap assembly 3910 in accordance with the present invention. The construction of the end cap assembly 3910 is similar to the construction of the end cap assembly 3410 shown in FIGS. 34-38, with the exception of the releasable battery door. Therefore, detailed description of the same or similar components of the end cap assembly will be omitted. As in the end cap assembly of FIGS. 34-38, the end cap assembly 3910 of this embodiment enables a suction tube to be connected via an end cap suction port 3926. The end cap suction port 3926, when connected with the suction tube, transfers all of the suction up through the handle via a smoke evacuation channel and out to the tip of the retractor. In accordance with this embodiment of the present invention, a number of features are provided on or together with the end cap assembly 3910 to maximize the suction efficiency and/or eliminate or reduce air leakage at or around the end cap assembly 3910 and/or the handle portion of retractor.

In one exemplary embodiment, an outer cover 3912 of the end cap assembly 3910 includes two main openings through which air may pass. As shown in FIGS. 39 and 40A-40C, the end cap assembly 3910 includes a first opening which connects with the end cap suction port 3926 and a second opening that is provided for an activation switch 3914 to be controlled externally. In this embodiment, the end cap assembly 3910 includes a battery assembly 4010 that is positioned directly over the activation switch and associated circuitry and wiring so as to prevent or reduce air leaks through the second opening in the outer cover 3912. Like the embodiment of the end cap assembly 3410 in FIGS. 34-38, this embodiment of the end cap assembly 3910 frees up the first opening connected to the end cap suction port for a stronger suction and covers up the second opening for the activation switch to prevent air leakage therethrough.

Figure 40A:
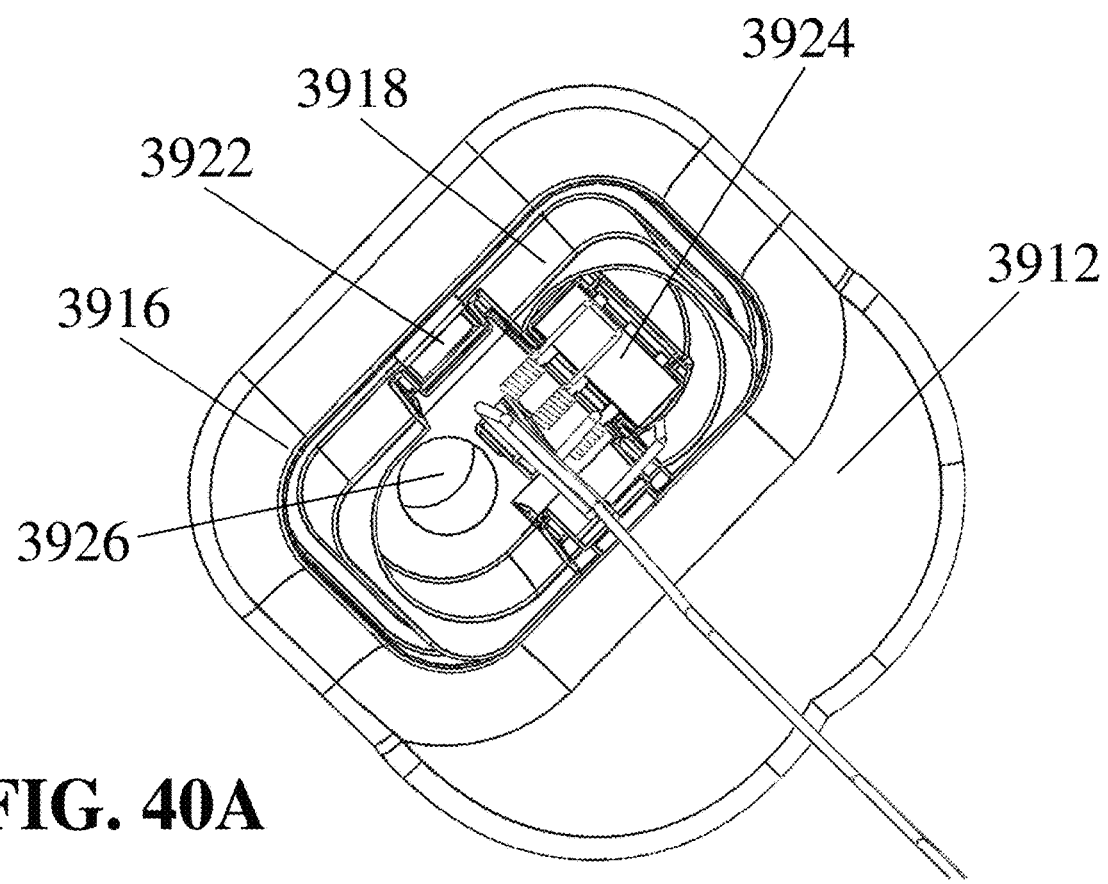
FIG. 40A-40B are internal views of the end cap assembly of FIG. 39 with additional features for providing an air tight seal.
Figure 40B:
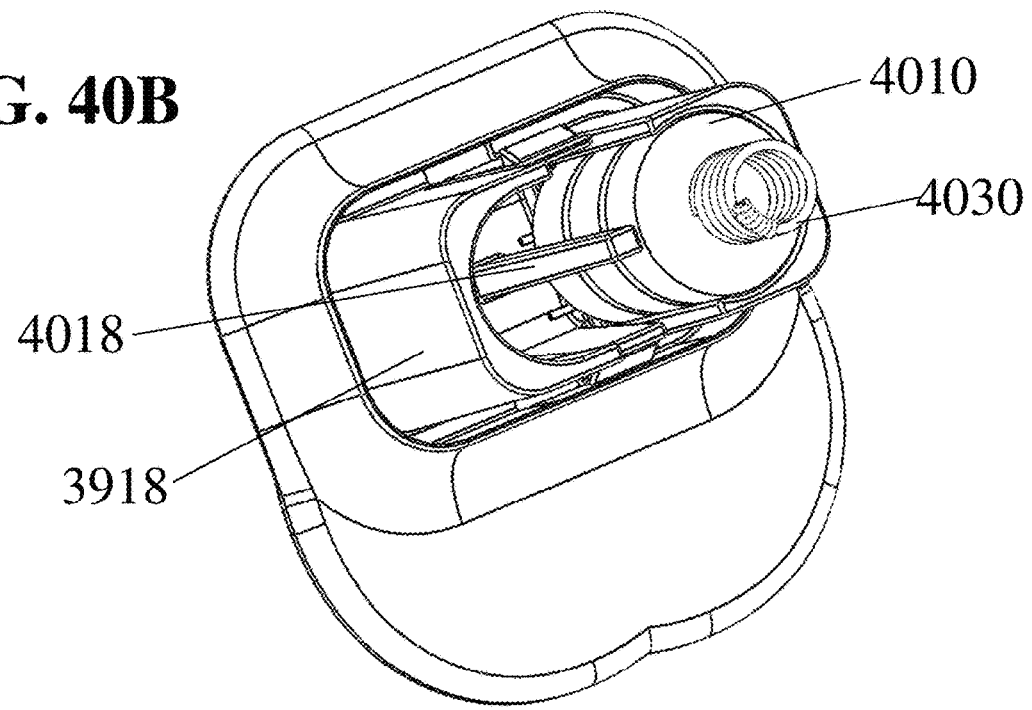

As shown in FIG. 40B, one or more batteries of the battery assembly 4010 are partially enclosed by an inner wall structure 3918, which also encloses or partially encloses a region adjacent to the battery assembly 4010 and in communication with the suction port 3926. In this illustrative embodiment, an internal projection 4018 or an additional wall structure is provided between the battery assembly and the suction region to hold the one or more batteries in place to prevent shifting or movement of the one or more batteries held by the end cap assembly.

Figure 40C:
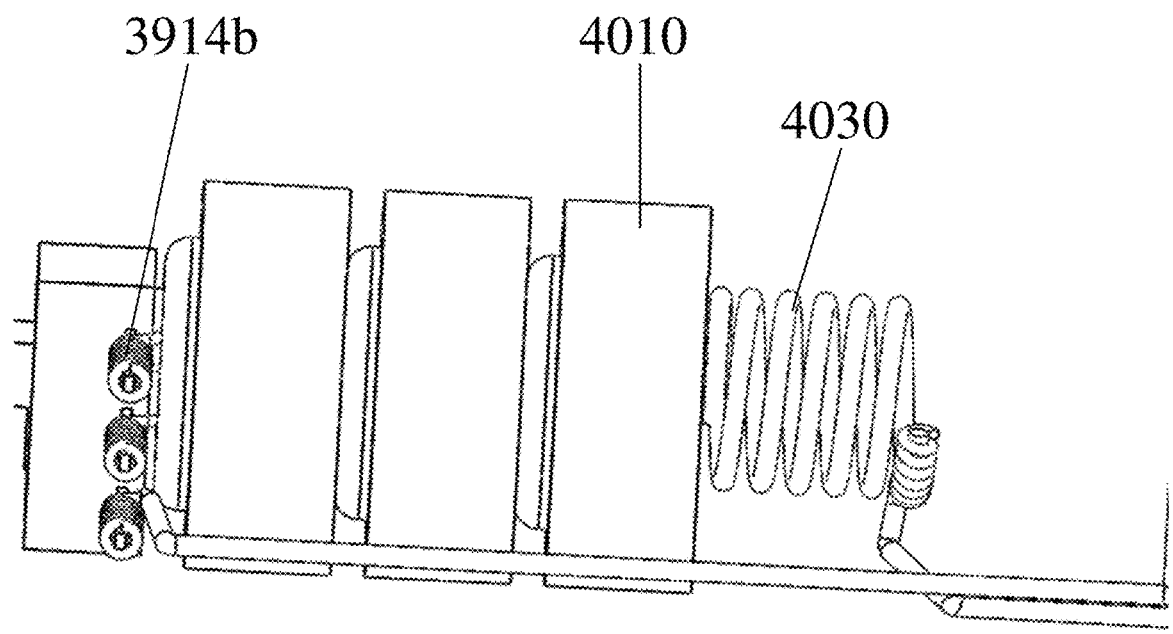
FIG. 40C shows a battery assembly and an activation switch housed by the end cap assembly of FIG. 39.

As further shown in FIGS. 40A-40C, the one or more batteries of the battery assembly 4010 are in direct contact with an electrical contact plate 3924 and in electrical contact with wire loops 3414*b* on one side and in direct and electrical contact with a spring 4030 on the other side. The spring is generally anchored to a post inside the retractor handle (not shown) in order to keep it in place. Specifically, the batteries are firmly pressed up against the electrical contact plate 3924 covering the activation switch 3914 so as to provide airtight sealing to the second opening.

Figure 41:
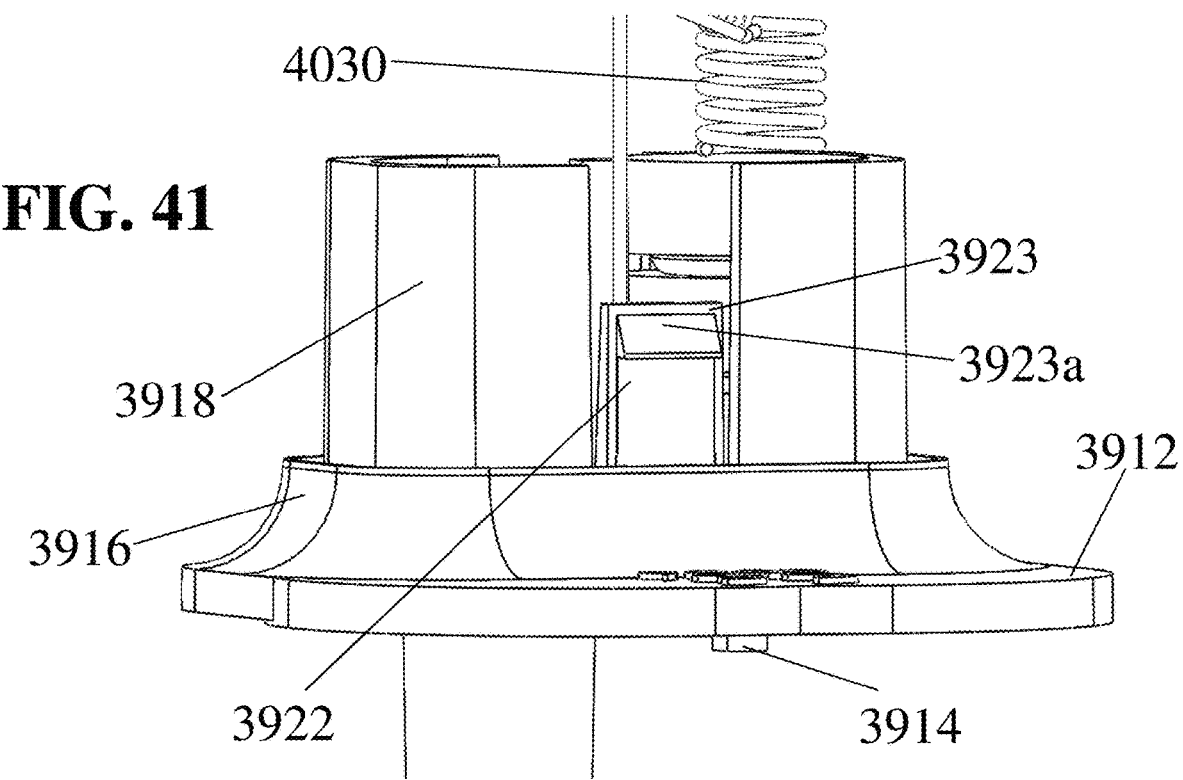
FIG. 41 is a side view of the end cap assembly of FIG. 39 showing a latch for locking with a retractor handle.
Figure 42:
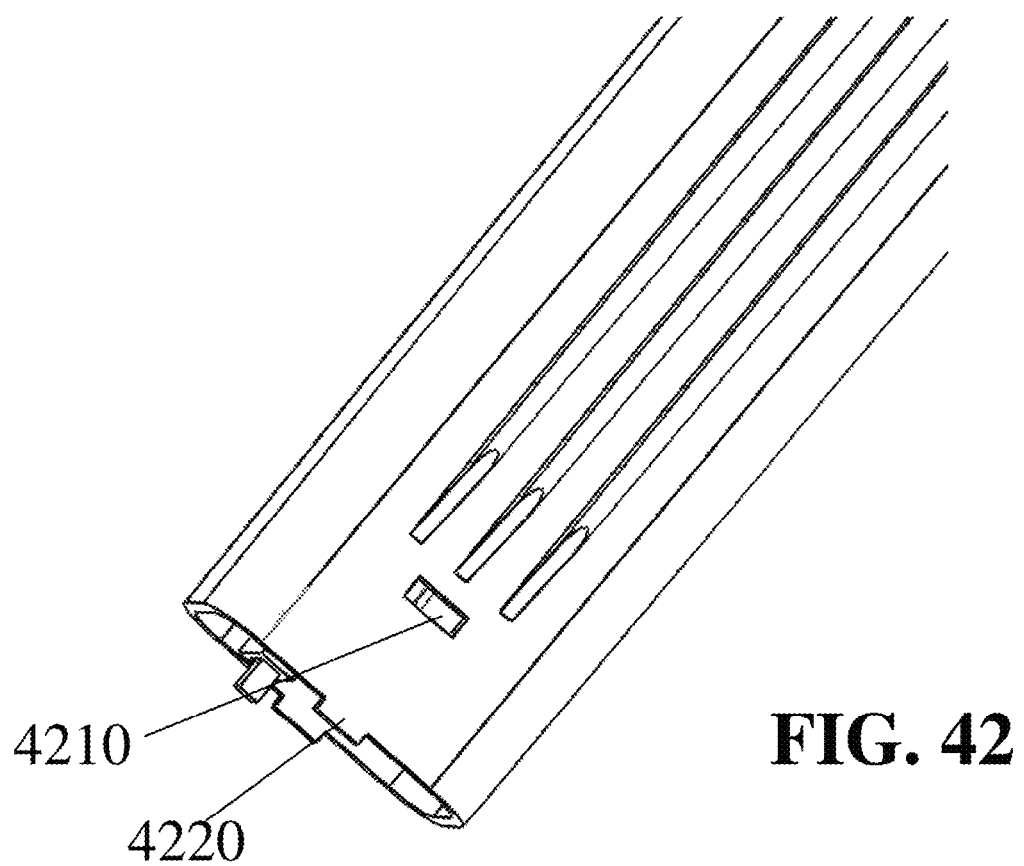
FIG. 42 is a partial view of a retractor handle showing an opening for receiving the latch from an end cap assembly.
Figure 43:
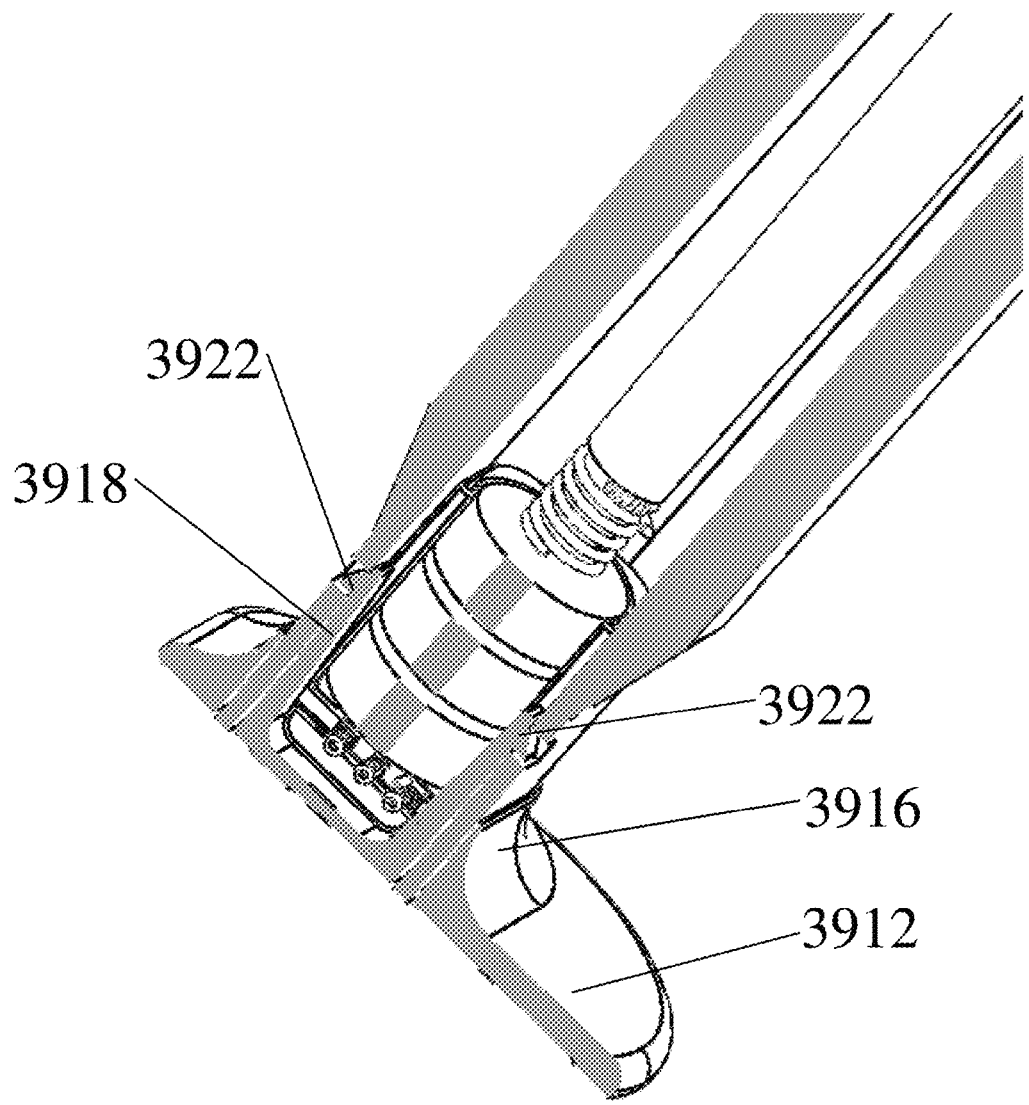
FIG. 43 is a cross-sectional view the end cap assembly of FIG. 39 coupled to a retractor handle to create an air tight seal.

In some embodiments, the airtight sealing is further improved by providing one or more latches 3922 on the end cap assembly 3910 for coupling the end cap assembly with the retractor handle. As shown in FIG. 41, the end cap assembly includes at least one latch 3922 molded thereon, and as in the embodiment of FIGS. 34-38, the one or more latches 3922 are provided between portions of the inner wall structure 3918 or may be incorporated into the inner wall structure 3918. The one or more latches 3922 on the end cap assembly 3910 are adapted to engage with one or more corresponding openings 4210 provided in the retractor handle shown in FIG. 42. In certain embodiments, molding of the latches 3922 requires formation of cutouts in the outer cover 3912 of the end cap assembly 3910, which are visible in FIG. 39, so that the mold can create the bottom portion of the latches. These cutouts are filled by respective protrusions 4220, shown in FIG. 42, which are provided on the bottom of the retractor handle. FIG. 43 shows a cross sectional view of the end cap assembly 3910 engaged with the retractor handle to illustrate the coupling between the end cap assembly 3910 and the retractor handle.

The construction of each latch 3922 shown in FIG. 41 also promotes airtightness when the end cap assembly 3910 is engaged with the retractor handle. Specifically, the latch 3922 comprises a post 3923 with a protrusion 3923*a* formed on its outward facing surface, wherein the protrusion 3923*a* has a smaller width and extends to a smaller height than the respective width and height of the post 3923. That is, the span of the post 3923 in the width direction and in the height direction is greater than the span of the protrusion 3923*a* so that the outer edge of the post 3923 forms a flange. In addition, the span of the post in the width and height direction is greater than the span of the corresponding opening in the retractor handle. In this way, when the protrusion 3923*a* is engaged with the corresponding opening 4210 in the retractor handle, the flange, which extends beyond the width and height of the protrusion 3923*a*, overlaps with any openings that may be formed around the area of engagement between the protrusion 3923*a* and the opening 4210. In this way, any possible air leaks through the openings 4210 in the handle are reduced or eliminated.

The end cap assemblies of FIGS. 34-43 are used with an illuminated surgical retractor that includes a smoke evacuation feature and provide airtight coupling with a vacuum source so as to provide more efficient suction to remove debris and smoke from the operating end during use. It is also contemplated that these and similar end cap assemblies may be used with other medical devices, such as suction devices and other types of instruments, that have a hollow handle and require airtight provision of suction.

It should be understood that the foregoing relates to exemplary embodiments of the invention and that modifications may be made without departing from the spirit and scope of the claimed invention.

I claim:
1. An illuminated medical device, comprising:
 a blade portion having a proximal end and a distal end;
 a handle portion connected to the proximal end of the blade portion, the handle portion having a hollow cross-section and an open distal end;

an illumination assembly comprising at least one light source, a switch assembly for energizing the light source, and at least one battery for powering the light source;

an end cap assembly configured to attach to the open distal end of the handle portion, the end cap assembly accommodating the switch assembly and being configured to hold the at least one battery within the handle and to partially enclose at least two sides of the at least one battery; and a smoke evacuation channel provided on the blade portion and in communication with the hollow cross-section of the handle, wherein a portion of the switch assembly extends through an opening in the end cap assembly and the at least one battery is held by the end cap assembly to abut and overlap with the switch assembly and to overlap with the opening in the end cap assembly, and wherein the end cap assembly includes a vacuum port adapted to couple to a vacuum source and to provide suction to the smoke evacuation channel through the handle.

2. The illuminated medical device of claim 1, wherein the at least one battery is held by the end cap assembly so as to not overlap with the vacuum port.

3. The illuminated medical device of claim 1, wherein:
the end cap assembly comprises: an outer cover having a first surface facing outwardly and an opposing second surface, wherein the opening and the vacuum port are formed in the outer cover; an outer wall structure formed on the second surface of the outer cover; and an inner wall structure formed on the second surface of the outer cover, the outer wall structure and the inner wall structure being concentric with respect to each other, wherein the outer wall structure and the inner wall structure form a channel therebetween adapted to receive the open bottom end of the handle.

4. The illuminated medical device of claim 3, wherein the inner wall structure partially encloses the at least one battery.

5. The illuminated medical device of claim 4, further comprising a spring for biasing the at least one battery in a direction toward the outer cover.

6. The illuminated medical device of claim 4, wherein the switch assembly comprises an operation member extending through the opening and wiring electrically coupled with the at least one battery and with the at least one light source, wherein the wiring is provided between the outer cover and the at least one battery.

7. The illuminated medical device of claim 6, further comprising a spring for biasing the at least one battery in a direction toward the outer cover, wherein the spring is electrically coupled with the at least one light source.

8. The illuminated medical device of claim 3, wherein the end cap assembly further comprises at least one latch for engaging with a corresponding opening formed in the handle, and wherein the at least one latch is configured so as to prevent air leakage through the corresponding opening in the handle.

9. The illuminated medical device of claim 3, wherein each latch comprises a post and a protrusion formed on a surface of the post and wherein a span of the post is greater than a span of the protrusion and greater than a span of the corresponding opening in the handle.

10. The illuminated medical device of claim 1, wherein the end cap assembly comprises: an outer cover having a first surface facing outwardly and an opposing second surface, wherein a second opening and the vacuum port are formed in the outer cover; and a releasable battery door covering the second opening in the outer cover and configured for removal of the at least one battery from the illuminated medical device.

11. The illuminated medical device of claim 10, wherein:
the switch assembly is disposed adjacent to the releasable battery door and the portion of the switch assembly extends through the opening formed in the releasable battery door.

12. The illuminated medical device of claim 11, wherein the releasable battery door is opened by rotating relative to the outer cover.

13. The illuminated medical device of claim 1, wherein the illuminated medical device is a surgical retractor.

14. The illuminated medical device of claim 13, wherein the smoke evacuation channel extends at least from the distal end of said blade portion to the handle portion and wherein the at least one light source is partially enclosed by the smoke evacuation channel.

15. An illuminated medical device comprising:
a blade portion having a proximal end and a distal end;
a handle portion connected to the proximal end of the blade portion, the handle portion having a hollow cross-section and an open distal end;
an illumination assembly comprising at least one light source, a switch assembly for energizing the light source, and at least one battery for powering the light source; and
an end cap assembly sealingly coupled to the open distal end of the handle portion so as to prevent or reduce air leakage around the end cap assembly, the end cap assembly holding and partially enclosing the at least one battery within the handle,
wherein the end cap assembly includes an outer cover configured to cover the open distal end of the handle portion, the cover including an opening formed therein for removal of the at least one battery from the illuminated retractor and a releasable door configured to cover the opening.

16. The illuminated medical device in accordance with claim 15, wherein the releasable door is opened and closed by rotating relative to the outer cover.

17. The illuminated medical device in accordance with claim 15, wherein the at least one battery held by the end cap assembly abuts the releasable door.

18. The illuminated medical device in accordance with claim 15, wherein at least a portion of the switch assembly is disposed adjacent the releasable door and the at least one battery held by the end cap assembly abuts the switch assembly.

19. The illuminated medical device in accordance with claim 15, further comprising a spring for biasing the at least one battery in a direction of the releasable door.

20. The illuminated medical device in accordance with claim 15, wherein a portion of the switch assembly extends through an aperture in the releasable door and the at least one battery is held by the end cap assembly to overlap with the switch assembly and the aperture in the releasable door.

21. The illuminated medical device in accordance with claim 15, wherein the medical device is a retractor.

22. The illuminated medical device in accordance with claim 15, wherein the end cap assembly is configured to provide airtight sealing between the end cap assembly and the handle portion.

* * * * *